United States Patent
Lee et al.

(10) Patent No.: US 10,111,628 B2
(45) Date of Patent: Oct. 30, 2018

(54) X-RAY IMAGING APPARATUS AND METHOD FOR MARKING A LOCATION OF A SURGICAL TOOL ON A DISPLAYED IMAGE

(71) Applicant: SAMSUNG ELECTRONICS CO., LTD., Suwon-si (KR)

(72) Inventors: Jae Hak Lee, Yongin-si (KR); Dong Goo Kang, Hwaseong-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 343 days.

(21) Appl. No.: 14/596,601

(22) Filed: Jan. 14, 2015

(65) Prior Publication Data

US 2015/0196260 A1  Jul. 16, 2015

(30) Foreign Application Priority Data

Jan. 14, 2014  (KR) .................. 10-2014-0004466

(51) Int. Cl.
*A61B 6/00* (2006.01)
*A61B 6/12* (2006.01)
(Continued)

(52) U.S. Cl.
CPC ............... *A61B 6/12* (2013.01); *A61B 6/487* (2013.01); *A61B 6/504* (2013.01); *A61B 6/022* (2013.01); *A61B 6/405* (2013.01); *A61B 6/4035* (2013.01); *A61B 6/466* (2013.01); *A61B 2090/364* (2016.02); *A61B 2090/376* (2016.02)

(58) Field of Classification Search
None
See application file for complete search history.

(56) References Cited

U.S. PATENT DOCUMENTS 6,470,207 B1 * 10/2002 Simon .................... A61B 34/20
378/207
2003/0191394 A1 * 10/2003 Simon .................... A61B 6/481
600/473
(Continued)

FOREIGN PATENT DOCUMENTS

JP     2009-18184 A    1/2009

OTHER PUBLICATIONS

Okumura, H. et al., "3D Roadmapping in neuroendovascular procedures—an evaluation", MedicaMundi, vol. 54, No. 3, 2010, pp. 5-11.
(Continued)

*Primary Examiner* — Jonathan Cwern
(74) *Attorney, Agent, or Firm* — Sughrue Mion, PLLC

(57) ABSTRACT

An X-ray imaging apparatus is provided. The X-ray imaging apparatus includes an overlapping unit configured to overlap a 2-Dimensional (2D) blood vessel image with a 2D fluoroscopy image to acquire a 2D roadmap image corresponding to a first position, a detector configured to detect a location of a surgical tool from the 2D roadmap image corresponding to the first position, and detect a blood vessel corresponding to the location of the surgical tool from a 3-Dimensional (3D) blood vessel image, and a User Interface (UI) processor configured to mark the 2D roadmap image with the location of the surgical tool with an identifier in the detected blood vessel.

19 Claims, 20 Drawing Sheets

(51) Int. Cl.
*A61B 6/02* (2006.01)
*A61B 90/00* (2016.01)

(56) References Cited

U.S. PATENT DOCUMENTS

| | | | | |
|---|---|---|---|---|
| 2007/0189457 | A1* | 8/2007 | Deinzer | A61B 6/12 378/98.12 |
| 2007/0276216 | A1* | 11/2007 | Beyar | A61B 6/12 600/407 |
| 2008/0009715 | A1* | 1/2008 | Kukuk | A61B 6/481 600/425 |
| 2009/0022262 | A1* | 1/2009 | Ohishi | A61B 6/12 378/4 |
| 2009/0279767 | A1* | 11/2009 | Kukuk | G06T 7/0044 382/132 |
| 2011/0103666 | A1* | 5/2011 | Ohishi | A61B 6/463 382/131 |
| 2011/0319752 | A1* | 12/2011 | Steinberg | A61B 6/12 600/424 |
| 2012/0183189 | A1* | 7/2012 | Florent | A61B 6/02 382/128 |
| 2013/0101196 | A1* | 4/2013 | Florent | G06T 7/0024 382/131 |
| 2013/0230136 | A1* | 9/2013 | Sakaguchi | H04N 13/00 378/41 |

OTHER PUBLICATIONS

Ruijters, Daniel et al., "Validation of 3D Multimodality Roadmapping in Interventional Neuroradiology", Physics in Medicine and Biology, vol. 56, No. 16, Aug. 2011, pp. 5335-5354.

* cited by examiner

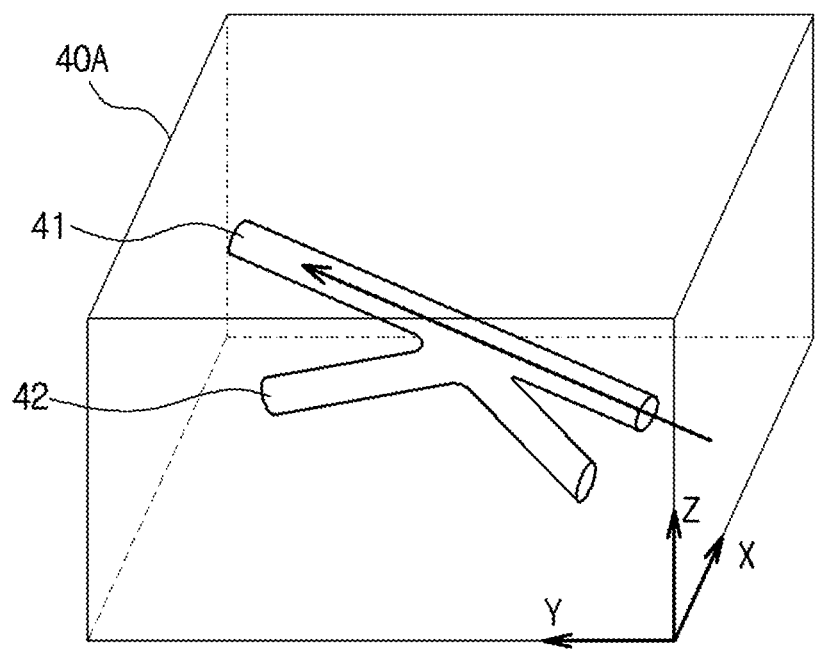

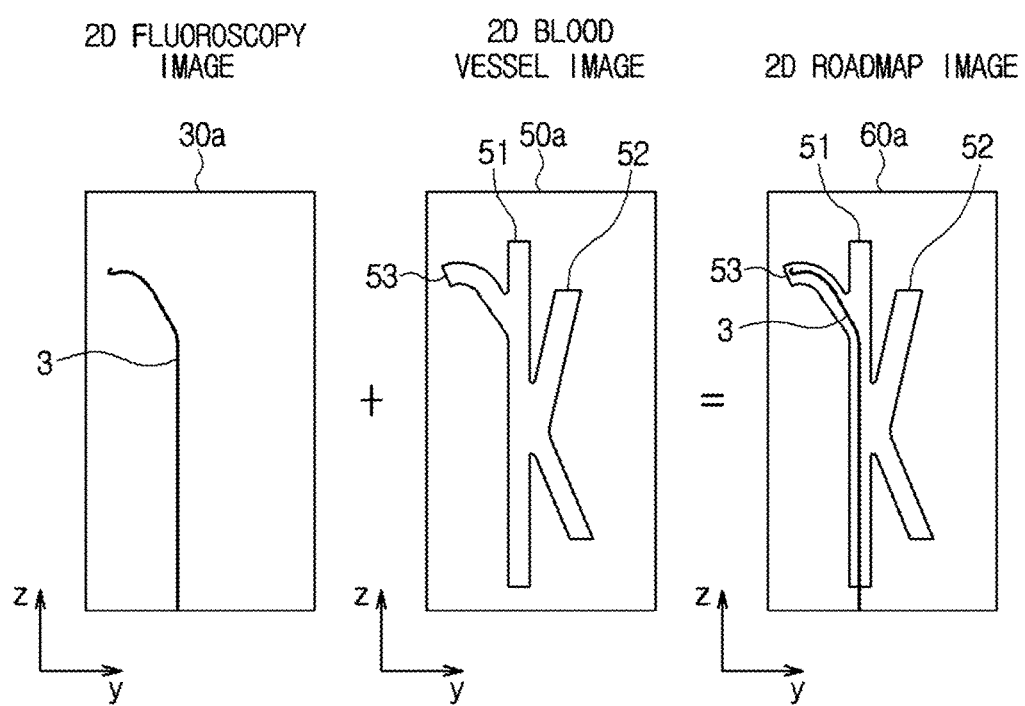

3D ROADMAP IMAGE

X-RAY IMAGING APPARATUS AND METHOD FOR MARKING A LOCATION OF A SURGICAL TOOL ON A DISPLAYED IMAGE

CROSS-REFERENCE TO RELATED APPLICATION

This application claims priority from Korean Patent Application No. 10-2014-0004466, filed on Jan. 14, 2014 in the Korean Intellectual Property Office, the disclosure of which is incorporated herein by reference in its entirety.

BACKGROUND

1. Technical Field

Apparatuses and methods consistent with exemplary embodiments relate to an X-ray imaging apparatus for displaying information about a location of a catheter or a guide wire on a 3-Dimensional (3D) volume during angiography, and a control method of the X-ray imaging apparatus.

2. Description of the Related Art

An X-ray imaging apparatus irradiates X-rays toward a subject (e.g., a human body or an object) in order to acquire images of the inside of the subject. Generally, the X-ray imaging apparatus is used to detect an abnormality such as lesions in human bodies in a medical field or the like, or to understand the inside structures of objects or elements. Also, the X-ray imaging apparatus is used to check baggage in an airport.

The X-ray imaging apparatus may include Digital Radiography (DR), Computed Tomography (CT), and Full Field Digital Mammography (FFDM).

The operation principle of an X-ray imaging apparatus is as follows. An X-ray imaging apparatus irradiates X-rays toward a subject (e.g., a human body or an object) and receives X-rays transmitted (or not transmitted) through the subject. Then, the X-ray imaging apparatus converts the received X-rays into electrical signals, and reads out the electrical signals to generate an X-ray image. The X-ray image is displayed through a display so that a user can understand the inside structure of the subject.

SUMMARY

According to an aspect of an exemplary embodiment, there is provided an X-ray imaging apparatus for displaying information about a location of a surgical tool, such as a catheter or a guide wire, on a 3-Dimensional (3D) volume during angiography, and a control method of the X-ray imaging apparatus.

Additional aspects of the disclosure will be set forth in part in the description which follows and, in part, will be obvious from the description, or may be learned by practice of the disclosure.

In accordance with an aspect of an exemplary embodiment, there is provided an X-ray imaging apparatus that includes an overlapping unit configured to overlap a 2-Dimensional (2D) blood vessel image with a 2D fluoroscopy image to acquire a 2D roadmap image corresponding to a first position, a detector configured to detect a location of a surgical tool from the 2D roadmap image corresponding to the first position, and detect a blood vessel corresponding to the location of the surgical tool from a 3-Dimensional (3D) blood vessel image, and a User Interface (UI) processor configured to mark the 2D roadmap image with the location of the surgical tool with an identifier in the detected blood vessel.

The X-ray imaging apparatus may further include an image producer configured to generate the 2D fluoroscopy image from irradiated X-rays from an X-ray generator located at the first position, an image reconstruction unit configured to generate a 3-Dimensional (3D) image of a subject, an image extraction unit configured to generate the 3D blood vessel image by extracting blood vessel information from the 3D image of the subject, and a projection unit configured to generate the 2D blood vessel image by projecting the 3D blood vessel image onto a 2D plane perpendicular to the first position.

The detector may be further configured to detect the location of the surgical tool and the blood vessel corresponding to the location of the surgical tool from the 2D roadmap image corresponding to the first position, and detect one or more blood vessel candidates corresponding to the detected blood vessel from the 3D blood vessel image.

If a blood vessel candidate is detected from the 3D blood vessel image, the detector may be further configured to determine that the detected blood vessel candidate is the blood vessel corresponding to the location of the surgical tool.

The X-ray imaging apparatus may further include a controller configured to move an X-ray generator from the first position to a second position in response to a plurality of blood vessel candidates being detected from the 3D blood vessel image.

The detector may be further configured to determine a blood vessel corresponding to the location of the surgical tool from among the plurality of blood vessel candidates, based on a second 2D roadmap image corresponding to the second position, and wherein the overlapping unit may be further configured to overlap a second 2D blood vessel image with a second 2D fluoroscopy image to acquire the second 2D roadmap image corresponding to the second position.

The X-ray imaging apparatus may further include an image producer configured to generate the second 2D fluoroscopy image from irradiated X-rays from the X-ray generator located at the second position, an image reconstruction unit configured to generate a 3-Dimensional (3D) image of a subject, an image extraction unit configured to generate a 3D blood vessel image by extracting blood vessel information from the 3D image of the subject, and a projection unit configured to generate the second 2D blood vessel image by projecting the 3D blood vessel image onto a 2D plane perpendicular to the second position.

The X-ray imaging apparatus may further include a controller configured to output an alarm for guiding an operator inserting the surgical tool into the subject if a plurality of blood vessel candidates are detected from the 3D blood vessel image.

If a plurality of blood vessel candidates are detected from the 3D blood vessel image, the UI processor may be further configured to display the plurality of blood vessel candidates differently from the remaining blood vessels in the 3D blood vessel image.

The X-ray imaging apparatus may further include a display configured to display at least one of the 2D fluoroscopy image, the 2D roadmap image, and a 3D roadmap image in which the location of the surgical tool is marked with an identifier in the detected blood vessel.

According to an aspect of another exemplary embodiment, there is provided a method of controlling an X-ray imaging apparatus, the method including overlapping a 2-Dimensional (2D) blood vessel image with a 2D fluoroscopy image to acquire a 2D roadmap image corresponding to a first position, detecting a location of a surgical tool from the 2D roadmap image corresponding to the first position, detecting a blood vessel corresponding to the location of the surgical tool from a 3-Dimensional (3D) blood vessel image, and marking the 2D roadmap image with the location of the surgical tool with an identifier in the detected blood vessel.

The method may further include generating, using an image producer, the 2D fluoroscopy image from irradiated X-rays from an X-ray generator located at the first position, generating, using an image reconstruction unit, a 3-Dimensional (3D) image of a subject, generating, using an image extraction unit, the 3D blood vessel image by extracting blood vessel information from the 3D image of the subject, and generating, using a projection unit, the 2D blood vessel image by projecting the 3D blood vessel image onto a 2D plane perpendicular to the first position.

The detecting of the blood vessel corresponding to the location of the surgical tool from the 3D blood vessel image may include detecting the location of the surgical tool and the blood vessel corresponding to the location of the surgical tool from the 2D roadmap image corresponding to the first position, and detecting one or more blood vessel candidates corresponding to the detected blood vessel from the 3D blood vessel image.

The method may further include determining that the detected blood vessel candidate is the blood vessel corresponding to the location of the surgical tool in response to a blood vessel candidate being detected from the 3D blood vessel image.

The method may further include moving an X-ray generator from the first position to a second position in response to a plurality of blood vessel candidates being detected from the 3D blood vessel image, and determining a blood vessel corresponding to the location of the surgical tool from among the plurality of blood vessel candidates, based on a second 2D roadmap image corresponding to the second position.

The method may further include generating a second 2D fluoroscopy image from irradiated X-rays from the X-ray generator located at the second position, generating a 3-Dimensional (3D) image of a subject, generating a 3D blood vessel image by extracting blood vessel information from the 3D image of the subject, and generating the second 2D blood vessel image by projecting the 3D blood vessel image onto a 2D plane perpendicular to the second position.

The method may further include outputting an alarm for guiding an operator inserting the surgical tool into the subject in response to a plurality of blood vessel candidates being detected from the 3D blood vessel image.

The method may further include displaying a plurality of blood vessel candidates differently from the remaining blood vessels in the 3D blood vessel image in response to the plurality of blood vessel candidates being detected from the 3D blood vessel image.

Therefore, because a location of a catheter or a guide wire is displayed on a 3D volume during angiography, an operator can perform a delicate surgery while checking the location of the catheter or the guide wire.

BRIEF DESCRIPTION OF THE DRAWINGS

The above and/or other aspects of the disclosure will become apparent and more readily appreciated from the following description of exemplary embodiments, taken in conjunction with the accompanying drawings, in which:

FIGS. 6A, 6B, and 6C are views describing a method of producing a 3-Dimensional (3D) roadmap image when a blood vessel candidate is detected to correspond to a moving path of a surgical tool, according to an exemplary embodiment of the present disclosure;

FIGS. 7A, 7B, 7C, 7D, 7E, and 7F are views describing a method of producing a 3D roadmap image when a plurality of blood vessel candidates are detected to correspond to a moving path of a surgical tool, according to an exemplary embodiment of the present disclosure;

DETAILED DESCRIPTION

Figure 1:
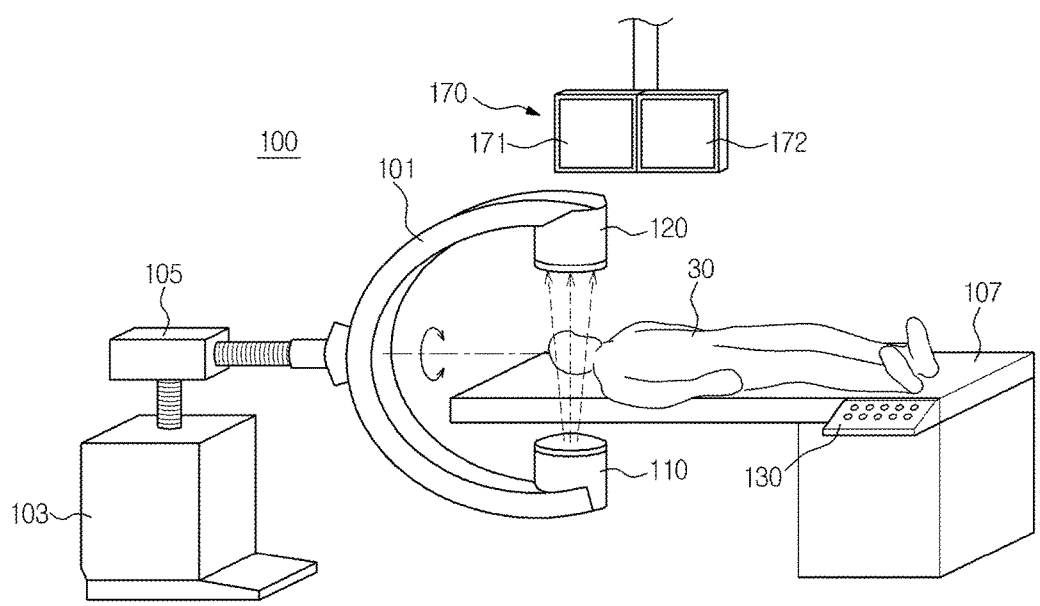
FIG. 1 is a perspective view of an X-ray imaging apparatus according to an exemplary embodiment of the present disclosure.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing operations described is an example; however, the sequence of and/or operations is not limited to that set forth herein and may be changed as is known in the art, with the exception of operations necessarily occurring in a particular order. In addition, respective descriptions of well-known functions and constructions may be omitted for increased clarity and conciseness.

Additionally, exemplary embodiments will now be described more fully hereinafter with reference to the accompanying drawings. The exemplary embodiments may, however, be embodied in many different forms and should not be construed as being limited to the embodiments set forth herein. These embodiments are provided so that this disclosure will be thorough and complete and will fully convey the exemplary embodiments to those of ordinary skill in the art. The scope is defined not by the detailed description but by the appended claims. Like numerals denote like elements throughout.

Hereinafter, an X-ray imaging apparatus and a control method thereof will be described with reference to the accompanying drawings, wherein like reference numerals refer to like elements throughout.

The X-ray imaging apparatus includes Digital Radiography (DR), Computed Tomography (CT), Full Field Digital Mammography (FFDM), and Fluoroscopy. In the following description, the X-ray imaging apparatus is assumed to be Fluoroscopy.

FIG. 1 is a perspective view of an X-ray imaging apparatus according to an embodiment.

Referring to FIG. 1, an X-ray imaging apparatus 100 may include a C-shaped arm 101, a main body 103, a connection axis 105, a table 107, an X-ray generator 110, an X-ray detector 120, an input unit 130, and a display 170.

The C-shaped arm 101 may be connected to the main body 103 through the connection axis 105. In both ends of the C-shaped arm 101, the X-ray generator 110 and the X-ray detector 120 may be disposed. The C-shaped arm 101 may rotate 360 degrees with respect to the connection axis 105. When the C-shaped arm 101 rotates with respect to the connection axis 105, the X-ray generator 110 and the X-ray detector 120 facing each other may rotate accordingly.

The table 107 may transfer a subject 30 that is to be X-ray scanned, between the X-ray generator 110 and the X-ray detector 120. The table 107 may move in front, back, left, right, up and down directions while keeping a horizontal state with respect to the ground.

By irradiating X-rays toward the subject 30 after locating the subject 30 between the X-ray detector 110 and the X-ray detector 120, an X-ray image may be acquired. According to an exemplary embodiment, the X-ray image may be a 2-Dimensional (2D) projection image or a 2D fluoroscopy image.

A 2D projection image may be acquired by irradiating X-rays toward the subject 30 one time after locating the X-ray generator 110 at a predetermined position. If X-rays are irradiated a plurality of times from the X-ray generator 110 toward the subject 30 when the C-shaped arm 101 is fixed, a plurality of the same 2D projection images may be acquired. If X-rays are irradiated toward the subject 30 whenever the X-ray generator 110 is located at predetermined positions by rotating the C-shaped arm 101 with respect to the connection axis 105, a plurality of different 2D projection images may be acquired. In the following description, a case in which a plurality of different 2D projection images of the subject 30 are acquired by irradiating X-rays to the subject 30 whenever the X-ray generator 110 is located at predetermined positions by rotating the C-shaped arm 101 with respect to the connection axis 105 will be described as an example.

A 2D fluoroscopy image may be acquired by continuing to irradiate X-rays toward the subject 30 from the X-ray generator 110 during a predetermined time period, for example, during angiography while the C-shaped arm 101 is fixed. Specifically, if the X-ray generator 110 continues to irradiate X-rays toward the subject 30 at a predetermined position, the X-ray detector 120 may continue to detect X-rays transmitted through the subject 30, and convert the detected X-rays into electrical signals. The electrical signals may be read at regular time intervals by an image producer 161 (see FIG. 5) of an image processor 160 (see FIG. 2), and whenever the electrical signals are read, a 2D projection image may be produced. The produced 2D projection images may be sequentially displayed by the display 170.

In summary, a 2D fluoroscopy image can be understood to be a moving image including a plurality of 2D projection images acquired by continuing to irradiate X-rays toward the subject 30 while the C-shaped arm 101 is fixed at a predetermined position.

The input unit 130 may receive instructions or commands for controlling operations of the X-ray imaging apparatus 100. To do this, the input unit 130 may include at least one of a keyboard, a mouse, a microphone, a camera sensor, and a foot pedal. According to an exemplary embodiment, the keyboard may be a hardwired implementation. In this case, the keyboard may include at least one of at least one direction key, at least one character key, and at least one knob. According to another exemplary embodiment, the keyboard may be a software implementation, like a Graphic User Interface (GUI) displayed on a touchscreen.

The display 170 may display an X-ray image of the subject 30. The X-ray image may be a 2D projection image, a 2D fluoroscopy image, a 3D blood vessel image, a 2D roadmap image, or a 3D roadmap image.

As described above, a plurality of 2D projection images of the subject 30 may be acquired by irradiating X-rays toward the subject 30 whenever the X-ray generator 110 is located at predetermined positions by rotating the C-shaped arm 101. The plurality of 2D projection images of the subject 30 may be acquired before angiography is performed. While the C-shaped arm 101 rotates, a fluorescent agent may be put into the blood vessels of the subject 30. Putting a fluorescent agent into the blood vessels of the subject 30 will make blood vessels appear in the plurality of 2D projection images. According to an exemplary embodiment, image reconstruction may be performed based on the plurality of 2D projection images, and if image reconstruction is completed, 3D volumes about the inside structure of the subject 30, for example, bones and blood vessels of the subject 30 may be reconstructed. Also, 3D volumes about the blood vessels may be extracted from the reconstructed 3D volumes.

A 2D fluoroscopy image may be a moving image consisting of a plurality of 2D projection images acquired by continuing to irradiate X-rays toward the subject 30 during angiography after fixing the X-ray generator 110 at a predetermined position. In the 2D fluoroscopy image, a surgical tool put into a blood vessel of the subject 30 may appear. During angiography, a fluorescent agent may be put into the blood vessels of the subject 30. If the fluorescent agent is put into the blood vessels of the subject 30, the blood vessels of the subject 30 appear in the 2D fluoroscopy image. However, because the fluorescent agent is put into the blood vessels for a short time, the blood vessels of the subject 30 may appear in the 2D fluoroscopy image for a short time only while the fluorescent agent is put into and persists within the blood vessels.

A 3D blood vessel image may be acquired by performing image reconstruction based on a plurality of different 2D projection images of the subject 30 to reconstruct a 3D volume of the subject 30, and then extracting blood vessel information from the 3D volume of the subject 30. Operations of reconstructing a 3D volume of the subject 30 and of producing a 3D blood vessel image of the subject 30 may be performed before angiography.

A 2D roadmap image may be acquired by projecting a 3D blood vessel image onto a 2D plane perpendicular to a first position to acquire a 2D blood vessel image, and then overlapping the 2D blood vessel image with a 2D fluoroscopy image. The 2D roadmap image may be displayed through the display 170. An operator may check a blood vessel into which a surgical tool has been put by viewing the 2D roadmap image.

A 3D roadmap image may be a 3D blood vessel image in which a moving path of a surgical tool, such as a catheter or a guide wire, is marked.

The display 170 may include at least one display. In FIG. 1, a case in which the display 170 includes a first display 171 and a second display 172 is shown. In this case, the first display 171 and the second display 172 may display different kinds of X-ray images. For example, the first display 171 may display a 2D roadmap image, and the second display 172 may display a 3D roadmap image.

According to an exemplary embodiment, the first display 171 may be a general display, and the second display 172 may be a Glass-free Stereoscopic 3D display. The Glass-free Stereoscopic 3D display enables a user to view 3D stereoscopic images without wearing 3D glasses.

The Glass-free Stereoscopic 3D display may be implemented by various methods. For example, the Glass-free Stereoscopic 3D display may be implemented by locating, in front of a display, a parallel barrier, a lenticular sheet in which lenticular lenses having a semi-cylindrical shape are arranged lengthwise, or a sheet in which micro lenses having a hemispherical shape are arranged side by side lengthwise and widthwise.

According to another exemplary embodiment, the display 170 may include three or more displays. In this case, the individual displays may display a 2D fluoroscopy image, a 2D roadmap image, and a 3D roadmap image, respectively.

If the display 170 includes a display, the screen of the display may be divided into a plurality of areas, and the divided areas may respectively display different kinds of images. Kinds of X-ray images that are to be displayed through the display 170, and a method of displaying X-ray images may be set by an operator. Also, the operator may change setting values during X-ray diagnosis.

Figure 2:
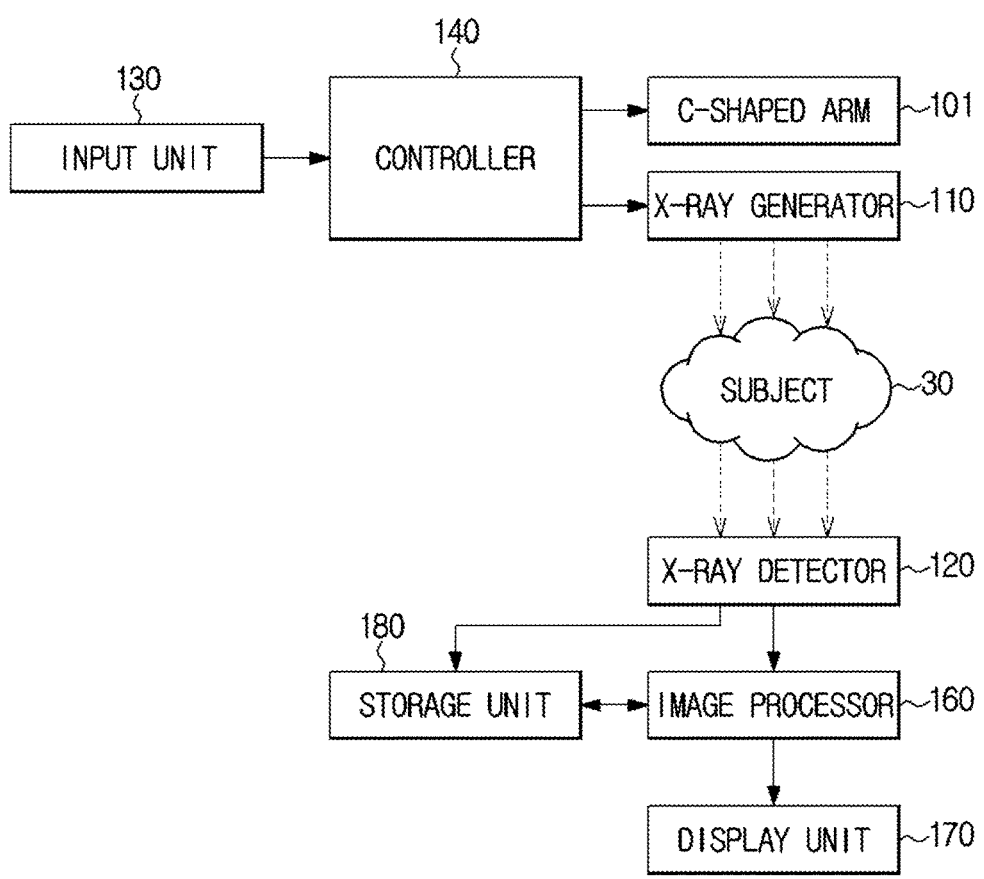
FIG. 2 is a control configuration view of an X-ray imaging apparatus according to an exemplary embodiment of the present disclosure.

FIG. 2 is a control configuration view of the X-ray imaging apparatus 100 according to an exemplary embodiment of the present disclosure.

Referring to FIG. 2, the X-ray imaging apparatus 100 may include the C-shaped arm 101, the X-ray generator 110, the X-ray detector 120, the input unit 130, a controller 140, an image processor 160, the display 170, and a storage unit 180.

The input unit 130 may receive, as described above, instructions or commands for controlling operations of the X-ray imaging apparatus 100 from an operator. For example, the input unit 130 may receive a command for adjusting the location of the table 107 (see FIG. 1), a command for starting diagnosis, a command for rotating the C-shaped arm 101, and a command for selecting a mode. The mode may include a fluoroscopy mode, a Digital Subtraction Angiography (DSA) mode, a 2D roadmapping mode, and a 3D roadmapping mode.

Fluoroscopy is an imaging technique of irradiating X-rays toward a subject to acquire a real-time moving image about the inside structure of the subject using a fluoroscope. Fluoroscopy may be used when an operator wants to view a surgical tool while monitoring an area to be treated in a subject, or when there is no need to monitor blood vessels.

DSA is a method of acquiring an X-ray image using a television camera before and after a contrast medium is inserted, digitalizing the X-ray image, performing subtraction on the X-ray image using two digital memory devices to remove bones or soft tissue from the X-ray image, and extracting a contrasted blood vessel image. According to the DSA, an image having high contrast resolution can be acquired with a small amount of contrast medium.

2D roadmapping is a technique of overlapping a blood vessel image acquired using X-rays with an image of a surgical tool acquired using X-rays. The 2D roadmapping is used to determine the location relation between surgical tools, the location relation between blood vessels, and the location relation between surgical tools and blood vessels.

A 3D roadmapping mode is configured to show a location of a surgical tool, such as a catheter or a guide wire, in a 3D blood vessel image.

The controller 140 may connect and control the individual components of the X-ray imaging apparatus 100. For example, the controller 140 may control at least one of the C-shaped arm 101, the X-ray generator 110, the X-ray detector 120, and the image processor 160, based on a command received through the input unit 130.

The X-ray generator 110 may generate X-rays, and irradiate the X-rays toward the subject 30. The X-ray generator 110 may include an X-ray tube to generate X-rays. The X-ray tube will be described in more detail with reference to FIG. 3, below.

Figure 3:
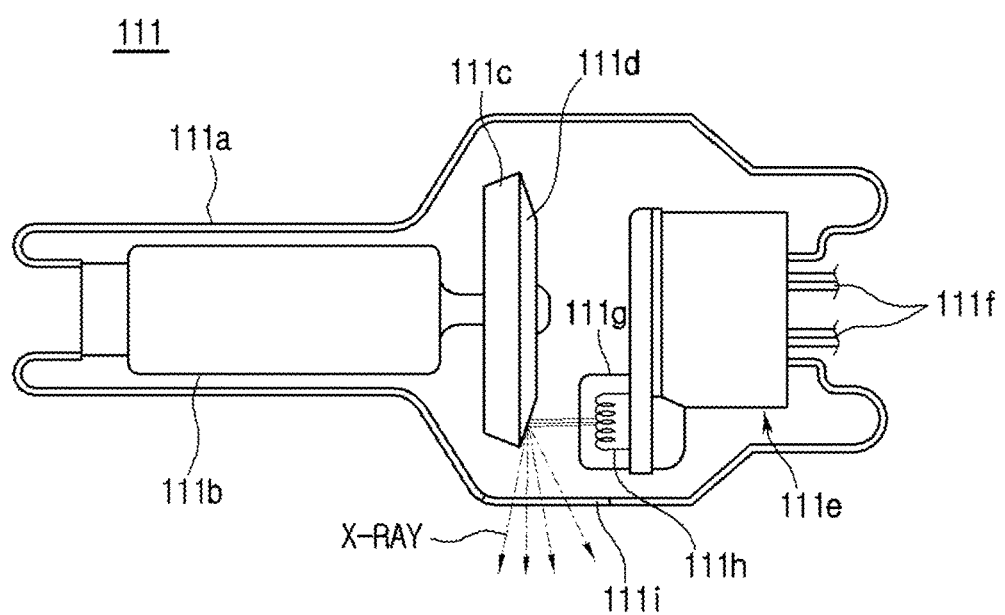
FIG. 3 illustrates a cross sectional view of an internal structure of an X-ray tube included in an X-ray generator according to an exemplary embodiment.

FIG. 3 illustrates a structure of an X-ray tube 111 included in the X-ray generator 110.

Referring to FIG. 3, the X-ray tube 111 may be embodied as a two-electrode vacuum tube including an anode 111c and a cathode 111e. The body of the two-electrode vacuum tube may be a glass tube 111a made of silica (hard) glass or the like.

The cathode 111e may include a filament 111h and a focusing electrode 111g for focusing electrons, and the focusing electrode 111g is also called a focusing cup. The inside of the glass tube 111a may be evacuated to a high vacuum state of about 10 mmHg, and the filament 111h of the cathode 111e may be heated to a high temperature, thereby generating thermoelectrons. The filament 111h may be a tungsten filament, and the filament 111h may be heated by applying a current to electrical leads 111f connected to the filament 111h. However, instead of the filament 111h, a carbon nano-tube capable of being driven with high-speed pulses may be used as the cathode 111e.

The anode 111c may be made of copper, and a target material 111d is applied on the surface of the anode 111c facing the cathode 111e, wherein the target material 111d may be a high-resistance material, e.g., Cr, Fe, Co, Ni, W, or Mo. The higher the melting point of the target material 111d, the smaller the focal spot size.

When a high voltage is applied between the cathode 111e and the anode 111c, thermoelectrons may be accelerated and collide with the target material 111d of the anode 111c, thereby generating X-rays. The X-rays may be irradiated to the outside through a window 111i. The window 111i may be a Beryllium (Be) thin film. A filter may be disposed ahead of or behind the window 111i in order to filter a specific band of energy.

The target material 111d may be rotated by a rotor 111b. When the target material 111d rotates, the heat accumulation rate may increase 10 times per unit area and the focal spot size may be reduced, compared to when the target material 111d is fixed.

The voltage that is applied between the cathode 111e and the anode 111c of the X-ray tube 111 is called a tube voltage. The magnitude of a tube voltage may be expressed as a crest value (kVp).

When the tube voltage increases, velocity of thermoelectrons may increase accordingly. Then, energy (energy of photons) of X-rays that are generated when the thermoelectrons collide with the target material 111d may also increase. If the energy of X-rays increases, a dose of X-rays that are transmitted through the subject 30 may increase accordingly. If the transmission dose of X-rays increases, a dose of X-rays that are detected by the X-ray detector 120 may increase. As a result, an X-ray image having a high Signal to Noise Ratio (SNR), that is, a high quality of X-ray image may be obtained.

In contrast, when the tube voltage decreases, velocity of thermoelectrons may decrease accordingly, and energy (energy of photons) of X-rays that are generated when the thermoelectrons collide with the target material 111*d* may also decrease. If the energy of X-rays decreases, a dose of X-rays that are absorbed in the subject 30 may increase, and a dose of X-rays that are detected by the X-ray detector 120 may decrease. As a result, an image having a low SNR, that is, a low quality of X-ray image may be obtained.

A current flowing through the X-ray tube 111 is called a tube current, and can be expressed as an average value (mA). When a tube current increases, a dose of X-rays (that is, the number of X-ray photons) may increase, and an X-ray image having a high SNR may be obtained. In contrast, if a tube current decreases, a dose of X-rays may decrease, and an X-ray image having a low SNR may be obtained.

In summary, energy of X-rays can be controlled by adjusting a tube voltage. Also, a dose of X-rays or an intensity of X-rays can be controlled by adjusting a tube current and an X-ray exposure time. By adjusting a tube voltage and a tube current according to the kind or properties of the subject 30, energy and a dose of X-rays that are irradiated may be controlled.

X-rays that are irradiated by the X-ray source 110 have a predetermined band of energy, and the predetermined band of energy may be defined by upper and lower limits. The upper limit of the predetermined band of energy, that is, a maximum energy of X-rays that are irradiated may be adjusted by the magnitude of a tube voltage. The lower limit of the predetermined band of energy, that is, a minimum energy of X-rays that are irradiated may be adjusted by a filter included in the X-ray source 110. By filtering a low energy band of X-rays using the filter, an average energy of X-rays that are irradiated may increase. Further, energy of X-rays that are irradiated may be expressed as a maximum energy or an average energy.

Referring again to FIG. 2, the X-ray detector 120 may detect X-rays transmitted through the subject 30, and convert the detected X-rays into electrical signals. The X-ray detector 120 will be described in more detail with reference to FIG. 4, below.

Figure 4:
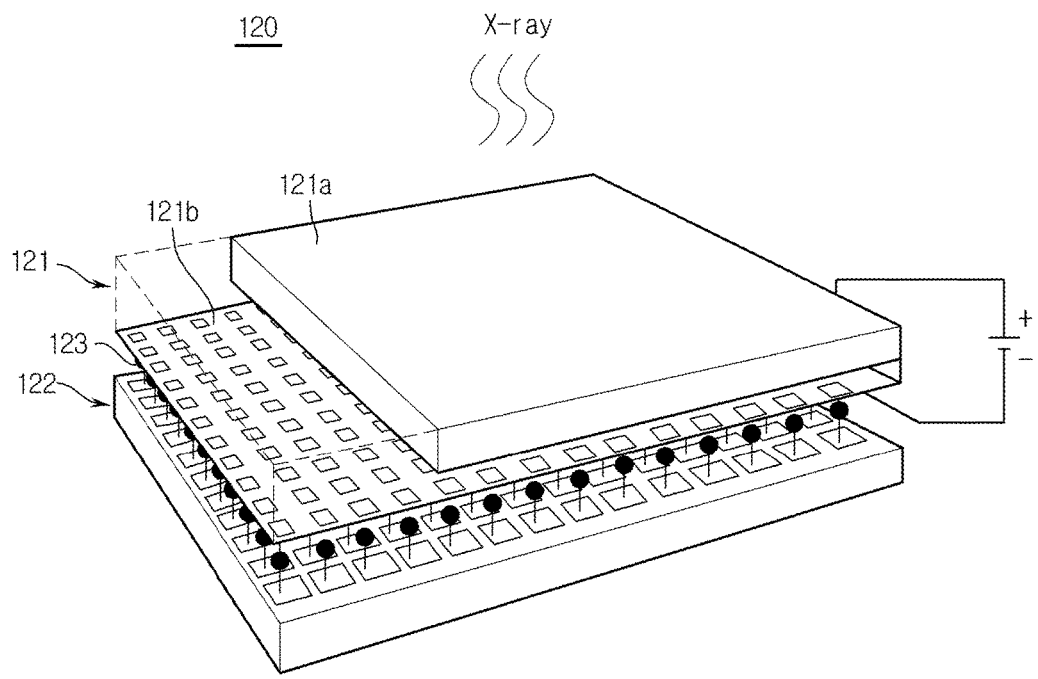
FIG. 4 illustrates a structure of an X-ray detector according to an exemplary embodiment.

FIG. 4 illustrates a structure of the X-ray detector 120.

Referring to FIG. 4, the X-ray detector 120 may include a light receiving device 121 to detect X-rays and convert the X-rays into electrical signals, and a read circuit 122 to read out the electrical signals. The read circuit 122 may have a 2D pixel array structure including a plurality of pixels. The light receiving device 121 may be made of a single crystal semiconductor material in order to ensure high resolution, high response speed, and a high dynamic area even under conditions of low energy and a small dose of X-rays. The single crystal semiconductor material may be Ge, CdTe, CdZnTe, or GaAs.

The light receiving device 121 may be in the form of a PIN photodiode. The PIN photodiode may be fabricated by bonding a p-type semiconductor substrate 121*b* in the form of a 2D pixel array on the lower surface of a n-type semiconductor substrate 121*a* having high resistance. The read circuit 122, which is fabricated according to a Complementary Metal Oxide Semiconductor (CMOS) process, may be coupled with the light receiving device 121 in units of pixels. The CMOS read circuit 122 and the light receiving device 121 may be coupled by a Flip-Chip Bonding (FCB) method. Specifically, the CMOS read circuit 122 and the light receiving device 121 may be coupled by forming bumps 123 with PbSn, In, or the like, reflowing, applying heat, and then compressing. The structure of the X-ray detector 120 is not limited to the example described above.

Referring again to FIG. 2, the image processor 160 may produce an X-ray image of the subject 30. The X-ray image may be a 2D projection image, a 2D fluoroscopy image, a 3D blood vessel image, a 2D roadmap image, or a 3D roadmap image. The image processor 160 will be described in more detail with reference to FIG. 5, below.

Figure 5:
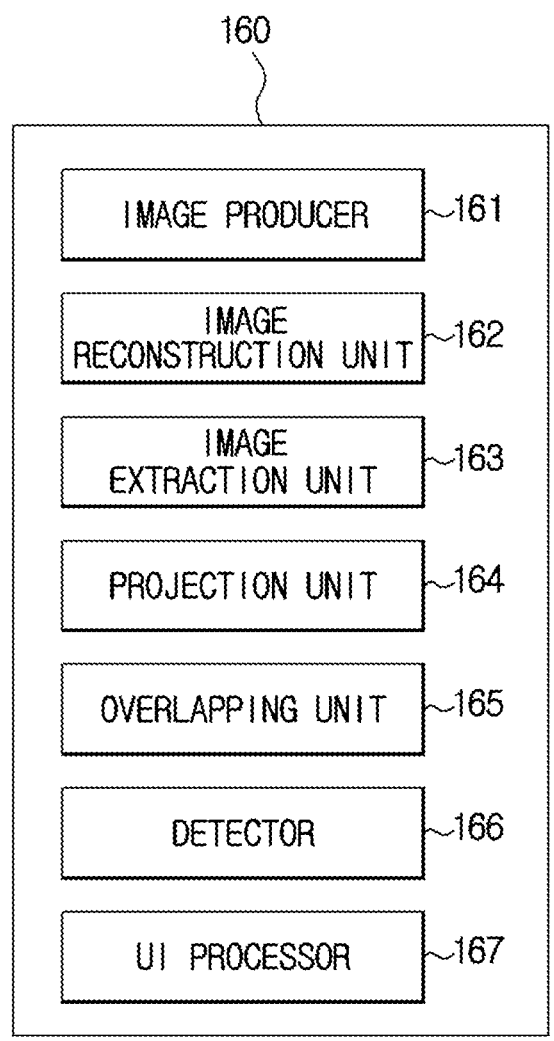
FIG. 5 is a block diagram illustrating an image processor according to an exemplary embodiment.

FIG. 5 is a block diagram illustrating the image processor 160.

As shown in FIG. 5, the image processor 160 may include an image producer 161, an image reconstruction unit 162, an image extraction unit 163, a projection unit 164, an overlapping unit 165, a detector 166, and a UI processor 167.

The image producer 161 may produce an X-ray image based on electrical signals output from the individual pixels of the X-ray detector 120 (see FIGS. 2 and 4). The X-ray image may be a 2D projection image or a 2D fluoroscopy image.

The 2D projection image may be produced based on X-rays transmitted through the subject 30 when X-rays are irradiated toward the subject 30 one time after the X-ray generator 110 is located at a first position. If X-rays are irradiated a plurality of times toward the subject 30 from the X-ray generator 110 located at the first position, 2D projection images corresponding to the number of times which X-rays were irradiated may be acquired. If X-rays are irradiated to the subject 30 whenever the X-ray generator 110 is located at predetermined positions while the X-ray generator 110 and the X-ray detector 120 rotate with respect to the subject 30, different 2D projection images corresponding to the number of times which X-rays were irradiated may be acquired.

The 2D fluoroscopy image may be produced based on X-rays transmitted through the subject 30 when X-rays continue to be irradiated to the subject 30 during a predetermined time period, for example, during a surgical procedure after the X-ray generator 110 is located at a first position. Specifically, if X-rays continue to be irradiated toward the subject 30, the X-ray detector 120 may continue to convert X-rays transmitted through the subject 30 into electrical signals, and the image producer 161 may read the electrical signals at predetermined time intervals to produce projection images. That is, a projection image can be understood to be a still image acquired by irradiating X-rays to the subject 30 when the X-ray generator 110 is located at a first position, and a fluoroscopy image can be understood to be a moving image consisting of projection images acquired at predetermined time intervals while X-rays are irradiated toward the subject 30 when the X-ray generator 110 is located at a first position.

The image reconstruction unit 162 may perform image reconstruction on a plurality of 2D projection images acquired at different positions. As a result, a 3D image in which a 3D volume of the subject 30 is reconstructed may be produced.

The image extraction unit 163 may extract an object of interest from the 3D image produced by the image reconstruction unit 162. For example, if the object of interest is blood vessels, the image extraction unit 163 may extract blood vessels from the 3D image to acquire a 3D blood vessel image. Coordinate information of blood vessels in a 3D space may be acquired from the 3D blood vessel image.

The projection unit 164 may project the 3D blood vessel image onto a 2D plane perpendicular to a first position, thereby acquiring a 2D blood vessel image. Also, the projection unit 164 may acquire a mapping table representing a mapping relationship between the locations of blood vessels in the 2D blood vessel image and the locations of the corresponding blood vessels in the 3D blood vessel image. When angiography begins, the X-ray generator 110 may be fixed at the first position, and continue to irradiate X-rays toward the subject 30 at the first position. As a result, a 2D projection image of the subject 30 may be acquired.

The overlapping unit 165 may overlap the 2D blood vessel image acquired from the result of the projection with the 2D fluoroscopy image. Thereby, a 2D roadmap image may be acquired. The 2D roadmap image may be displayed through the first display 171 of the display 170.

The detector 166 may detect a location of a surgical tool in the 2D roadmap image. Also, the detector 166 may detect a blood vessel corresponding to the location of the surgical tool in the 2D roadmap image. Also, the detector 166 may detect one or more blood vessel candidates corresponding to the blood vessel detected from the 2D roadmap image, from among blood vessels included in the 3D blood vessel image. At this time, the detector 166 may use the mapping table to detect the blood vessel candidates.

Specifically, if the locations of individual blood vessels in the 3D blood vessel image are expressed by x, y, and z values, the locations of individual blood vessels in the 2D blood vessel image acquired from the result of the projection are expressed by the x and y values. That is, the z values disappear due to projection. As such, because z values among coordinate values representing the locations of blood vessels in the 3D blood vessel image disappear, a plurality of blood vessel candidates may be detected from the 3D blood vessel image when a blood vessel corresponding to the location of the surgical tool in the 2D roadmap image is detected.

According to an exemplary embodiment, if a plurality of blood vessel candidates is detected from the 3D blood vessel image, the detector 166 may provide information about the blood vessel candidates to the controller 140. The controller 140 which has received the information about the blood vessel candidates may rotate the C-shaped arm 101 (see FIG. 2) to move the X-ray generator 110 from the first position to a second position. For example, the controller 140 may rotate the C-shaped arm 101 by 10 degrees. Then, the X-ray generator 110 and the X-ray detector 120 may rotate by the rotation angle of the C-shaped arm 101. The rotation angle of the C-shaped arm 101 may be set by an operator before X-ray scanning. That is, the rotation range of the C-shaped arm 101 is not limited to 10 degrees. For example, the C-shaped arm 101 may rotate by a predetermined angle between 10 degrees and 90 degrees.

After the X-ray generator 110 moves from the first position to the second position by rotating the C-shaped arm 101, the projection unit 164 may project the 3D blood vessel image onto a 2D plane based on the second position to thus acquire a new 2D blood vessel image and a new mapping table. The image producer 161 may acquire a 2D fluoroscopy image corresponding to the second position. Thereafter, the overlapping unit 165 may overlap the 2D fluoroscopy image acquired at the second position with the 2D blood vessel image acquired at the second position to thus produce a 2D roadmap image corresponding to the second position. Then, the detector 166 may detect a location of the surgical tool from the 2D roadmap image corresponding to the second position, detect a blood vessel corresponding to the location of the surgical tool from the 2D roadmap image, and detect one or more blood vessel candidates corresponding to the detected blood vessel from the 3D blood vessel image.

In summary, until one blood vessel candidate is detected from the 3D blood vessel image, operation of changing the position of the X-ray generator 110, acquiring a 2D roadmap image, detecting a location of the surgical tool from the 2D roadmap image, and detecting a blood vessel corresponding to the location of the surgical tool, and detecting one or more blood vessel candidates corresponding to the detected blood vessel from the 3D blood vessel image may be repeated.

If one blood vessel candidate is detected from the 3D blood vessel image by repeatedly performing the above-described operation, the detector 166 may select the blood vessel candidate as a blood vessel corresponding to the location of the surgical tool.

Instead of the method of changing the position of the X-ray generator 110, there is a method of guiding an operator to move a surgical tool until a blood vessel corresponding to the location of the surgical tool is clearly determined, detecting the location of the surgical tool from a 2D roadmap image acquired in real time when the surgical tool is moved, and then detecting one or more blood vessel candidates from a 3D blood vessel image based on the location of the surgical tool. The method will be described with reference to FIGS. 8A to 8D.

The UI processor 167 may create a user interface needed for interactions between the X-ray imaging apparatus 100 and the operator. More specifically, the UI processor 167 may display blood vessel candidates detected from a 3D blood vessel image and/or a blood vessel selected from the detected blood vessel candidates, differently from the other blood vessels. There are various methods for displaying blood vessel candidates detected from a 3D blood vessel image and/or a blood vessel selected from the detected blood vessel candidates, differently from the other blood vessels. For example, there are a method of displaying the corresponding blood vessels with a color that is different from that of the other blood vessels, and a method of displaying an identifier such as a dotted line around or in the corresponding blood vessels.

Also, the UI processor 167 may display a part (a part corresponding to the location of the surgical tool) of a blood vessel selected from the 3D blood vessel image, differently from the other blood vessels. For example, the UI processor 167 may display the color of a part corresponding to the location of the surgical tool, in a blood vessel selected from the 3D blood vessel image, differently from the color of the remaining part.

As another example, the UI processor 167 may mark the location of the surgical tool as an identifier, around or in a part corresponding to the location of the surgical tool, in a blood vessel selected from the 3D blood vessel image. The identifier may be a line. A shape (e.g., a solid line, a dotted line, a broken line, or an alternated long and short dash line) of the line, a thickness of the line, and a color of the line may be set in advance by the operator. In the following description, a case in which an identifier, such as a solid line or a dotted line, is displayed in the selected blood vessel will be described as an example.

A 3D blood vessel image in which blood vessel candidates corresponding to the location of a surgical tool are displayed differently from the other blood vessels, or a 3D blood vessel image in which the location of a surgical tool is marked as an identifier in a blood vessel selected from among blood vessel candidates corresponding to the location of the surgical tool can be considered as a 3D roadmap image.

Referring again to FIG. 2, the storage unit 180 may store various data and algorithms needed for operations of the X-ray imaging apparatus 100. For example, the storage unit 180 may store an algorithm needed for image reconstruction, and an algorithm needed for detecting the location of a surgical tool in a 2D fluoroscopy image. In addition, the storage unit 180 may store images output from the image processor 160, and mapping tables acquired from the results of projection.

The storage unit 180 may be a volatile memory device, a non-volatile memory device, a hard disk, an optical disk, or a combination of one or more of the above-mentioned devices. However, the storage unit 180 may be any other device well known in the art.

Referring again to FIG. 2, the display 170 may display an X-ray image produced by the image processor 160. For example, the display 170 may display at least one of a 2D fluoroscopy image, a 2D roadmap image, and a 3D roadmap image.

Hereinafter, a method of producing a 3D roadmap image in which a moving path of a surgical tool inserted into a blood vessel of the subject 30 is marked in a 3D blood vessel image will be described with reference to FIGS. 6A to 8D.

Figure 6A:
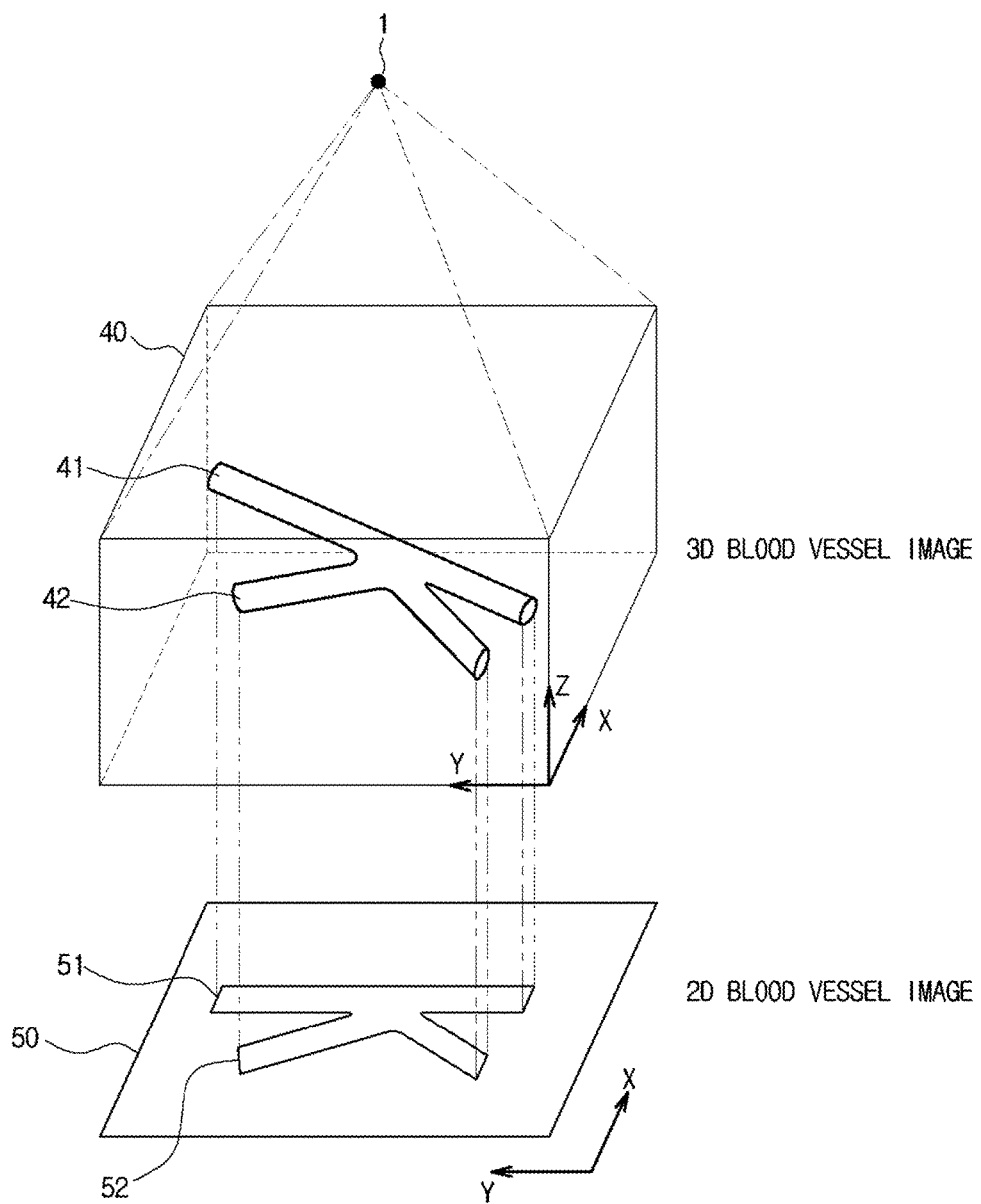
Figure 6B:
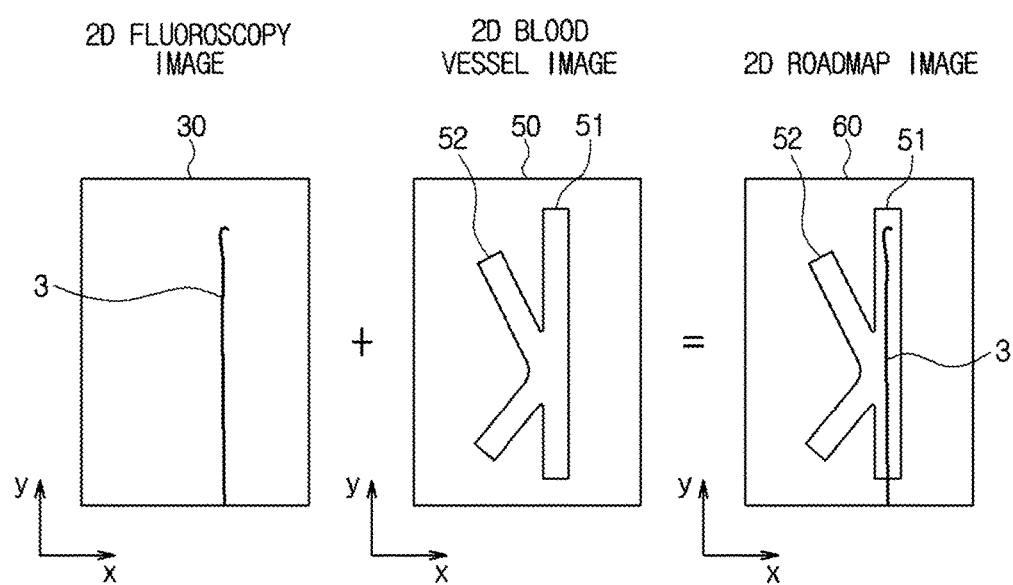

FIGS. 6A, 6B, and 6C are views for describing a method of producing a 2D roadmap image, and a method of producing a 3D roadmap image when a blood vessel candidate is detected to correspond to a moving path of a surgical tool in the 2D roadmap image, according to an exemplary embodiment of the present disclosure.

In FIG. 6A, a 3D blood vessel image 40 including a first blood vessel 41 and a second blood vessel 42 is shown. The 3D blood vessel image 40 may be acquired by performing image reconstruction based on a plurality of different 2D projection images about a subject to reconstruct a 3D volume of the subject, and extracting blood vessel information from the 3D volume of the subject, as described above. As shown in FIG. 6A, the 3D volume image 40 may be displayed in a 3D space composed of x-, y- and z-axes.

By projecting the 3D blood vessel image 40 onto a plane perpendicular to a predetermined position, a 2D blood vessel image may be acquired. In FIG. 6A, a case in which a 2D blood vessel image 50 including a first blood vessel 51 and a second blood vessel 52 is acquired by projecting the 3D blood vessel image 40 onto a xy plane perpendicular to a first position 1 is shown. Herein, the first blood vessel 51 of the 2D blood vessel image 50 corresponds to the first blood vessel 41 of the 3D blood vessel image 40, and the second blood vessel 52 of the 2D blood vessel image 50 corresponds to the second blood vessel 42 of the 3D blood vessel image 40.

Referring to FIGS. 2 and 6A, if angiography begins, the X-ray generator 110 may be fixed at the first position 1, and continue to irradiate X-rays toward the subject at the first position 1. In this state, if an operator inserts a surgical tool 3 into a blood vessel of the subject, a 2D fluoroscopy image 30 as shown in FIG. 6B may be acquired in real time. The 2D fluoroscopy image 30 shows only the surgical tool 3, and the reason is because no fluorescent agent has been put into blood vessels of the subject. Accordingly, by overlapping the 2D fluoroscopy image 30 shown in FIG. 6B with the 2D blood vessel image 50 shown in FIG. 6A to produce a 2D roadmap image 60, and displaying the 2D roadmap image 60 through the display 170, the operator can check a blood vessel into which the surgical tool 3 has been inserted.

According to an exemplary embodiment, the X-ray imaging apparatus 100 may produce a 3D roadmap image as well as the 2D roadmap image 60, and display the 3D roadmap image through the display 170. In order to produce a 3D roadmap image, first, a location of the surgical tool 3 may be detected from the 2D roadmap image 60. Then, a blood vessel corresponding to the location of the surgical tool 3 may be detected from the 2D roadmap image 60. For example, in the case of the 2D roadmap image 60 shown in FIG. 6B, the first blood vessel 51 may be detected as a blood vessel corresponding to the location of the surgical tool 3. Thereafter, blood vessel candidates corresponding to the first blood vessel 51 detected from the 2D roadmap image 60 may be detected from the 3D blood vessel image 40. For example, in the 3D blood vessel image 40 shown in FIG. 6A, the first blood vessel 41 may be detected as a blood vessel candidate corresponding to the first blood vessel 51 of the 2D roadmap image 60.

As such, if a blood vessel candidate is detected from the 3D blood vessel image 40, the detected blood vessel candidate may be determined as a blood vessel path corresponding to a moving path of the surgical tool 3. The moving path of the surgical tool 3 may be marked as an identifier in the determined blood vessel path. Referring to a 3D roadmap image 40A of FIG. 6C, a solid arrow is displayed in the first blood vessel 41.

The above-described example relates to a case in which a blood vessel candidate is detected to correspond to the moving path of the surgical tool 3 in the 3D blood vessel image 40. If a plurality of blood vessel candidates are detected to correspond to the moving path of the surgical tool 3 in the 3D blood vessel image 40, the X-ray imaging apparatus 100 may output an alarm to notify the operator that a plurality of blood vessel candidates have been detected. Then, the operator may change the position of the X-ray generator 110 (see FIG. 2) or keep inserting the surgical tool 3 into the blood vessel until a blood vessel candidate is determined to correspond to the moving path of the surgical tool 3. Hereinafter, a method of determining a blood vessel candidate from a plurality of blood vessel candidates detected from the 3D blood vessel image 40 will be described with reference to FIGS. 7A to 8D.

FIGS. 7A to 7F are views for describing a method of producing a 3D roadmap image when a plurality of blood vessel candidates are detected to correspond to the moving path of the surgical tool 3, according to an exemplary embodiment of the present disclosure.

Figure 7A:
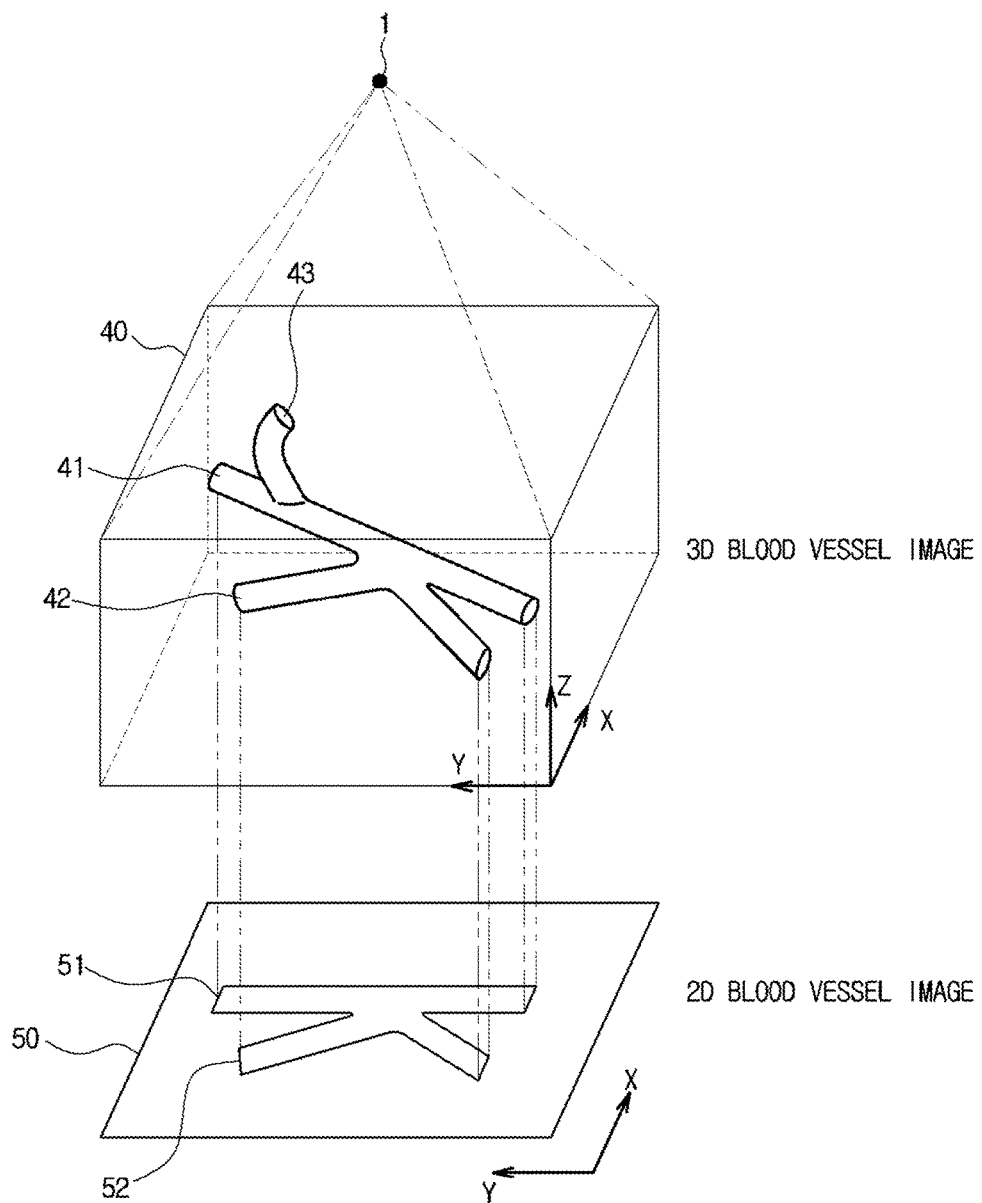

In FIG. 7A, a 3D blood vessel image 40 including a first blood vessel 41, a second blood vessel 42, and a third blood vessel 43 is shown. The third vessel 43 is assumed to have the same x and y coordinates as those of the first blood vessel 41, and a z coordinate different from that of the first blood vessel 41.

By projecting the 3D blood vessel image 40 shown in FIG. 7A onto a xy plane perpendicular to a first position 1, a 2D blood vessel image 50 including a first blood vessel 51 and a second blood vessel 52 may be acquired. The reason why the third blood vessel 43 of the 3D blood vessel image 40 does not appear in the 2D blood vessel image 50 is because the third blood vessel 43 has the same x and y coordinates as those of the first blood vessel 41.

Figure 7B:
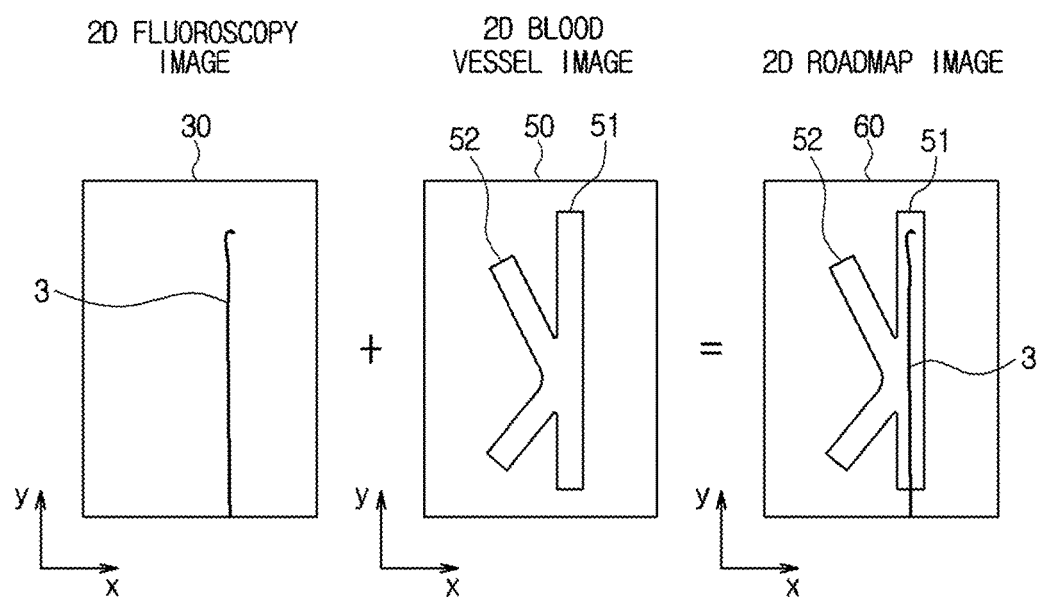

If angiography begins, the X-ray generator 110 (see FIG. 2) may be fixed at the first position 1, and continue to irradiate X-rays to the subject at the first position 1. In this state, if an operator inserts a surgical tool 3 into a blood vessel of the subject, a 2D fluoroscopy image 30 as shown in FIG. 7B may be acquired in real time. Then, by overlapping the 2D fluoroscopy image 30 with the 2D blood vessel image 50, a 2D roadmap image 60 as shown in FIG. 7B may be acquired. The 2D roadmap image 60 may be displayed through the display 170.

Thereafter, the X-ray imaging apparatus 100 may produce a 3D roadmap image, and display the 3D roadmap image through the display 170. More specifically, the location of the surgical tool 3 may be detected from the 2D roadmap image 60 as shown in FIG. 7B. Then, a blood vessel corresponding to the location of the surgical tool 30 may be detected from the 2D roadmap image 60. For example, in the case of the 2D roadmap image 60 as shown in FIG. 7B, the first blood vessel 51 may be detected as a blood vessel corresponding to the location of the surgical tool 3. Thereafter, blood vessel candidates corresponding to the first blood vessel 51 detected from the 2D roadmap image 60 may be detected from the 3D blood vessel image 40. For example, in the 3D blood vessel image 40 shown in FIG. 7A, the first blood vessel 41 and the third blood vessel 43 may be detected as blood vessel candidates corresponding to the first blood vessel 51 of the 2D roadmap image 60.

Figure 7C:
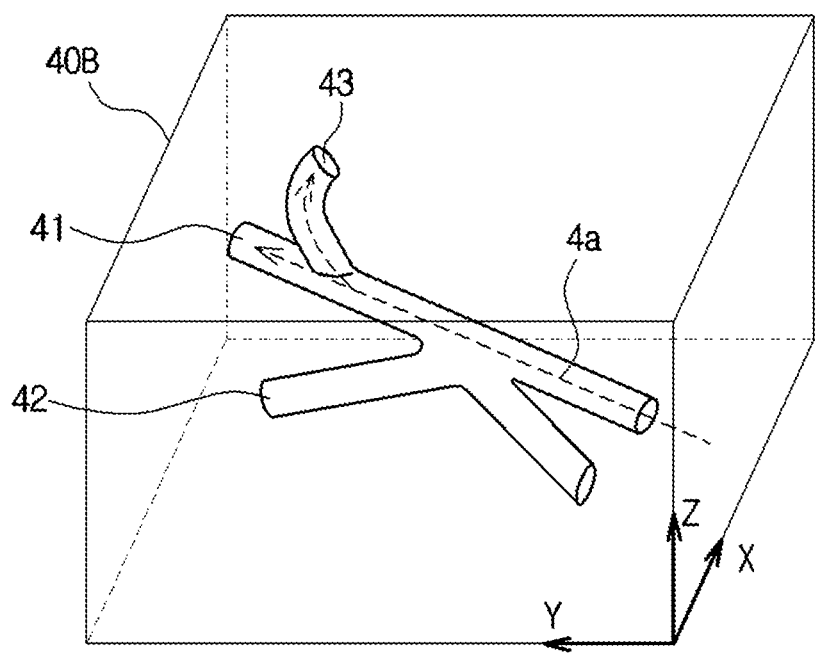

Then, identifiers may be displayed in all the detected blood vessel candidates to produce a 3D roadmap image 40B as shown in FIG. 7C. Referring to FIG. 7C, dotted arrows 4a are displayed in both the first blood vessel 41 and the third blood vessel 43. The 3D roadmap image 40B may be displayed through the display 170.

Thereafter, the X-ray imaging apparatus 100 may change the position of the X-ray generator 110. For example, the X-ray imaging apparatus 100 may move the X-ray generator 110 from the first position 1 to a second position 2.

Figure 7D:
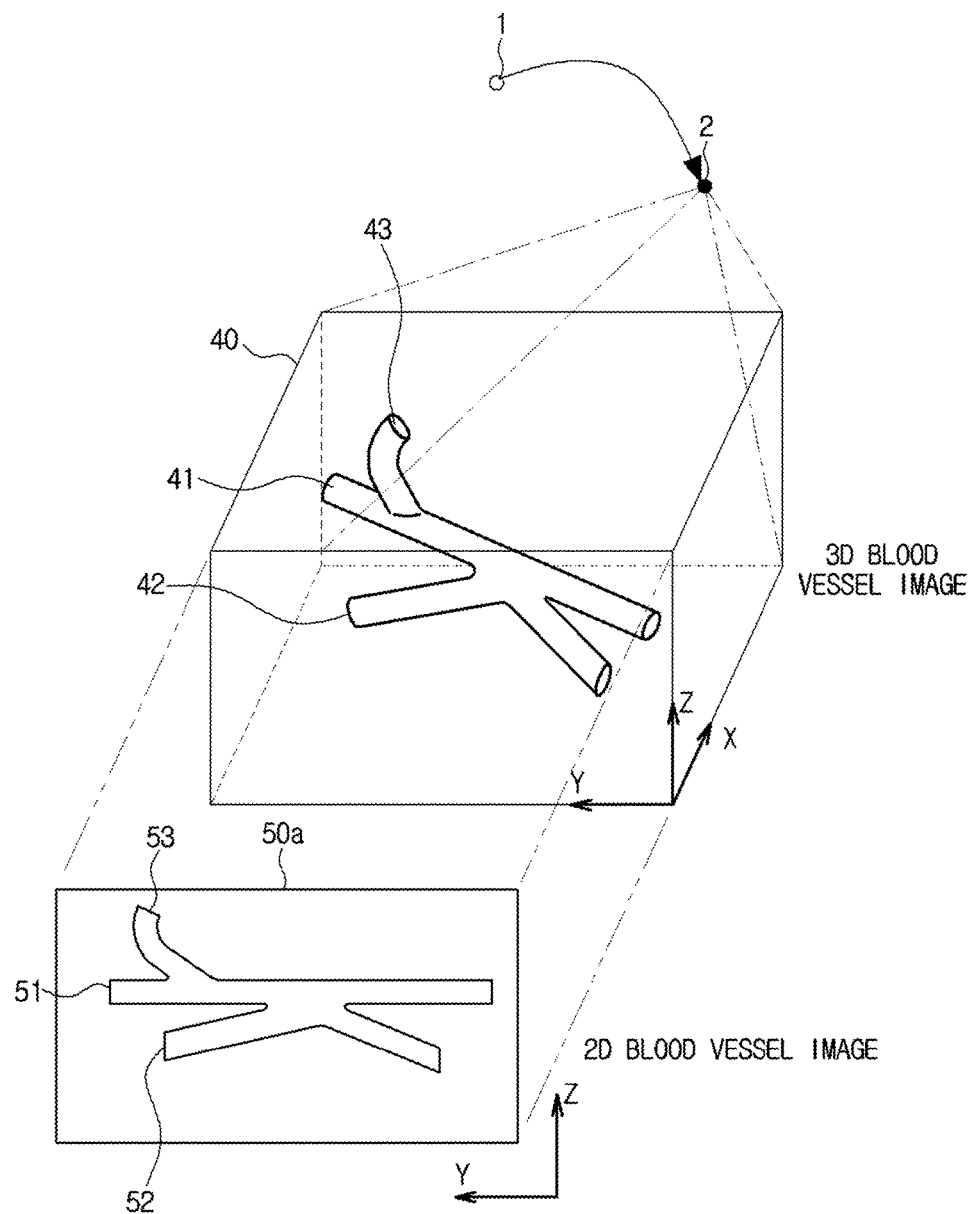

Then, the projection unit 164 (see FIG. 5) may project the 3D blood vessel image 40 onto a yz plane perpendicular to the second location 2 to thus produce a 2D blood vessel image 50a corresponding to the second position 2, as shown in FIG. 7D. Referring to FIGS. 7A and 7D, in the 2D blood vessel image 50a acquired at the second position 2, all of the first blood vessel 51, the second blood vessel 52, and the third blood vessel 53 are shown, unlike the 2D blood vessel image 50 acquired at the first position 1. The first blood vessel 51, the second blood vessel 52, and the third blood vessel 53 included in the 2D blood vessel image 50a respectively correspond to the first blood vessel 41, the second blood vessel 42, and the third blood vessel 43 of the 3D blood vessel image 40.

After the X-ray generator 110 moves from the first position 1 to the second position 2, the X-ray generator 110 may continue to irradiate X-rays toward the subject. As a result, a 2D fluoroscopy image 30a corresponding to the second position 2 may be acquired, as shown in FIG. 7E. Referring to FIGS. 7B and 7E, the location of the surgical tool 3 in the 2D fluoroscopy image 30 acquired when the X-ray generator 110 is located at the first position 1 is different from the location of the surgical tool 3 in the 2D fluoroscopy image 30a acquired when the X-ray generator 110 is located at the second position 2.

Thereafter, the overlapping unit 165 (see FIG. 5) may overlap the 2D fluoroscopy image 30a acquired at the second position 2 with the 2D blood vessel image 50a acquired at the second position 2 to thus produce a 2D roadmap image 60a corresponding to the second position 2, as shown in FIG. 7E. Comparing the 2D roadmap image 60 of FIG. 7B to the 2D roadmap image 60a of FIG. 7E, the 2D roadmap image 60 of FIG. 7B does not show an exact blood vessel into which the surgical tool 3 has been inserted, whereas the 2D roadmap image 60a of FIG. 7E shows the third blood vessel 53 into which the surgical tool 3 has been inserted.

Then, the detector 166 (see FIG. 5) may detect the location of the surgical tool 3 from the 2D roadmap image 60a corresponding to the second position 2, and detect a blood vessel corresponding to the location of the surgical tool 3. In the case of the 2D roadmap image 60a as shown in FIG. 7E, the third blood vessel 53 may be detected as a blood vessel corresponding to the location of the surgical tool 3. Then, a blood vessel candidate corresponding to the third blood vessel 53 detected from the 2D roadmap image 60a may be detected from the 3D blood vessel image 40. For example, in the 3D blood vessel image 40 shown in FIG. 7A, the third blood vessel 43 may be detected as a blood vessel candidate corresponding to the third blood vessel 53 of the 2D roadmap image 60a.

Figure 7F:
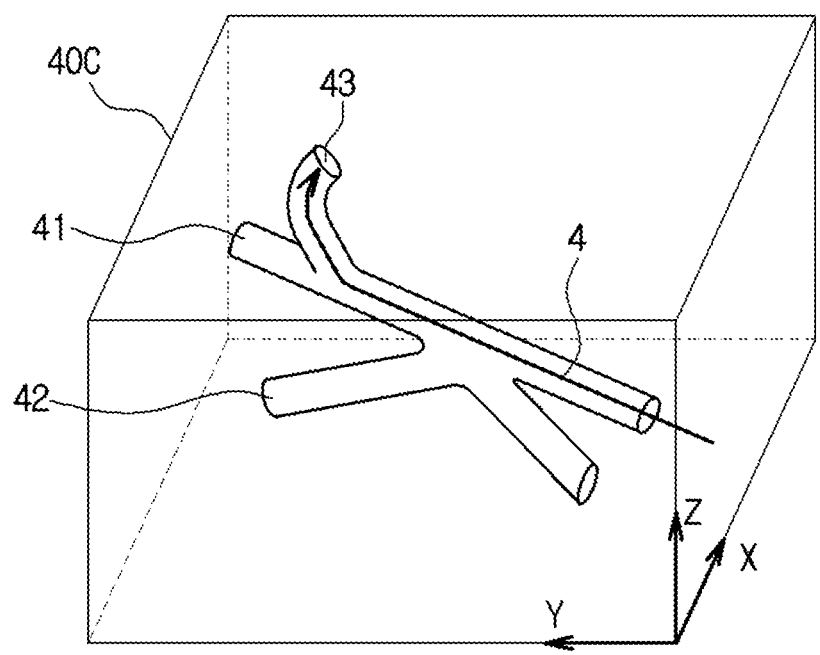

The detected blood vessel candidate may be determined as a blood vessel path corresponding to a moving path of the surgical tool 3. The UI processor 167 (see FIG. 5) may mark the moving path of the surgical tool 3 as an identifier in the determined blood vessel path. Referring to a 3D roadmap image 40C of FIG. 7F, a solid line 4 is displayed in the third blood vessel 43. If the 3D roadmap image 40C of FIG. 7F is displayed through the display 170, the operator can accurately check the moving path of the surgical tool 3.

FIGS. 8A to 8D are views for describing a method of producing a 3D roadmap image when a plurality of blood vessel candidates are detected to correspond to a moving path of a surgical tool, according to another exemplary embodiment of the present disclosure.

Figure 8A:
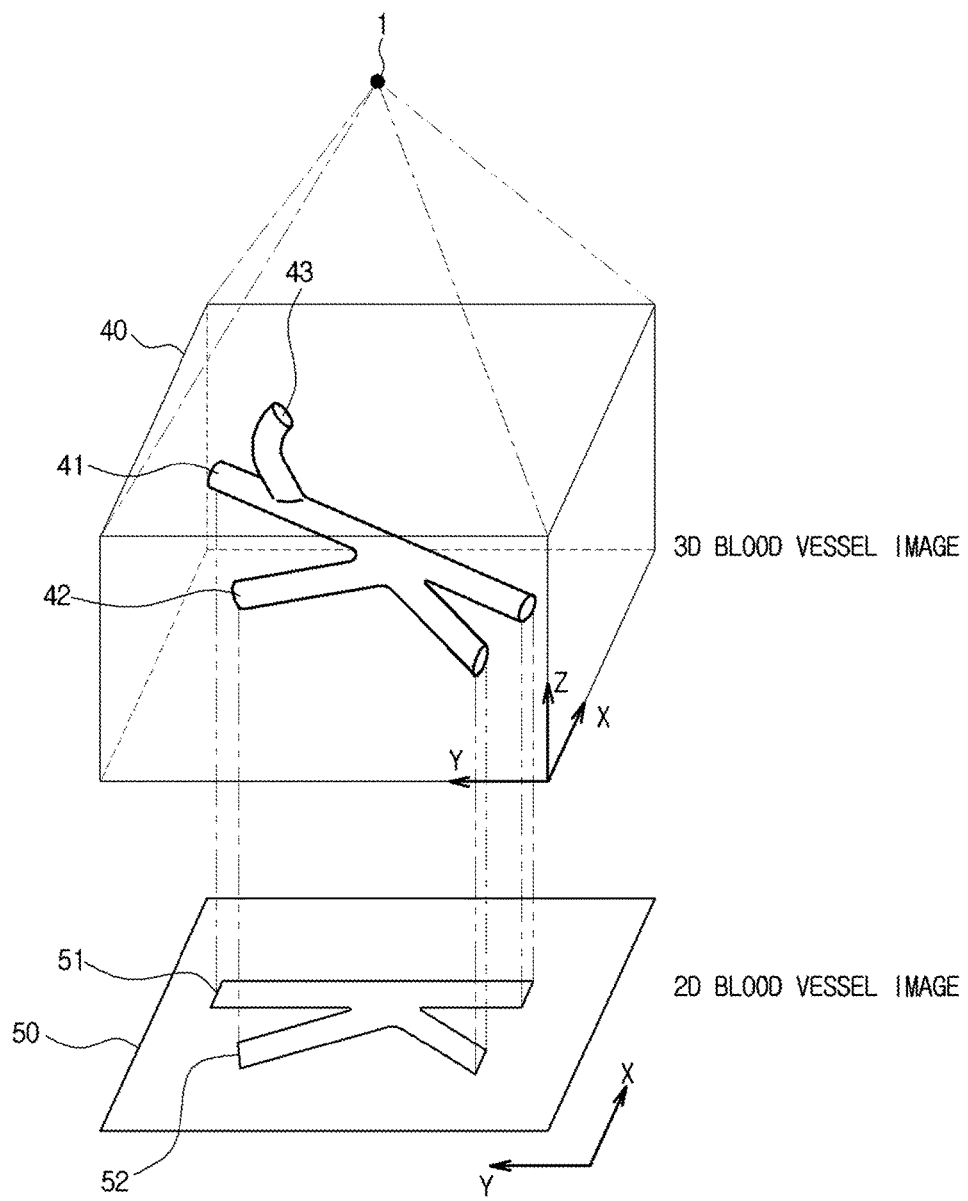
FIGS. 8A, 8B, 8C, and 8D are views describing a method of producing a 3D roadmap image when a plurality of blood vessel candidates are detected to correspond to a moving path of a surgical tool, according to another exemplary embodiment of the present disclosure.

In FIG. 8A, a 3D blood vessel image 40 including a first blood vessel 41, a second blood vessel 42, and a third blood vessel 43 is shown. The third blood vessel 43 is assumed to have the same x and y coordinates as those of the first blood vessel 41 and a z coordinate different from that of the first blood vessel 41.

The 3D blood vessel image 40 shown in FIG. 8A may be projected onto a xy plane perpendicular to a first location 1, so that a 2D blood vessel image 50 including a first blood vessel 51 and a second blood vessel 52 may be acquired.

Figure 8B:
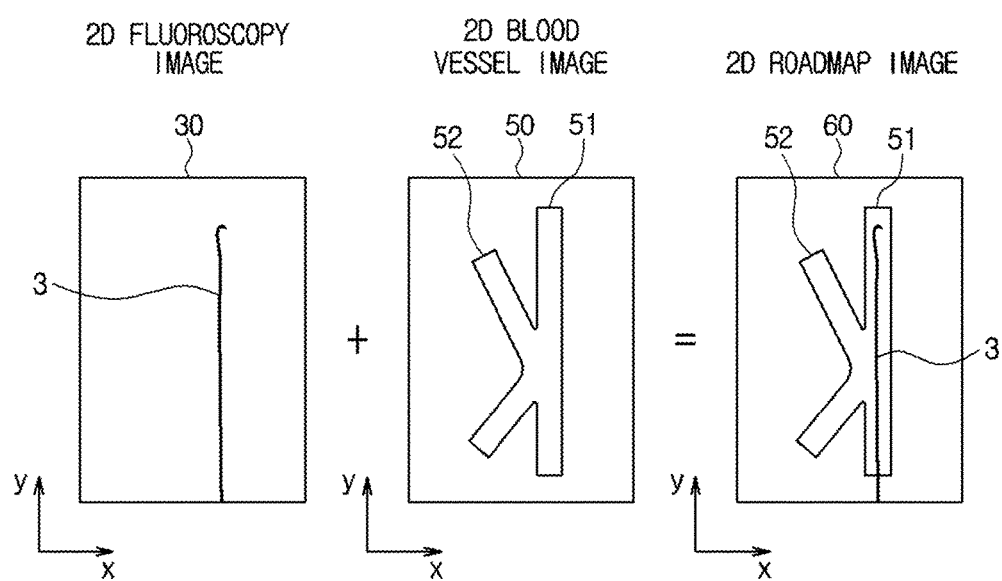

If an operator inserts a surgical tool 3 into a blood vessel of a subject while the X-ray generator 110 (see FIG. 2) continues to irradiate X-rays to the subject, a 2D fluoroscopy image 30 as shown in FIG. 8B may be acquired in real time. Then, by overlapping the 2D fluoroscopy image 30 with the 2D blood vessel image 50, a 2D roadmap image 60 as shown in FIG. 8B may be acquired.

In the 2D roadmap image 60 of FIG. 8B, the first blood vessel 51 may be detected as a blood vessel corresponding to the location of the surgical tool 3. Then, one or more blood vessel candidates corresponding to the first blood vessel 51 detected from the 2D roadmap image 60 may be detected from the 3D blood vessel image 40. In the 3D blood vessel image 40 shown in FIG. 8A, the first blood vessel 41 and the third blood vessel 43 may be detected as blood vessel candidates corresponding to the first blood vessel 51 of the 2D roadmap image 60.

If a plurality of blood vessel candidates is detected, identifiers may be displayed in all the plurality of blood vessel candidates. For example, dotted arrows may be displayed in the plurality of blood vessel candidates, that is, in the first blood vessel 41 and the third blood vessel 43.

Figure 8C:
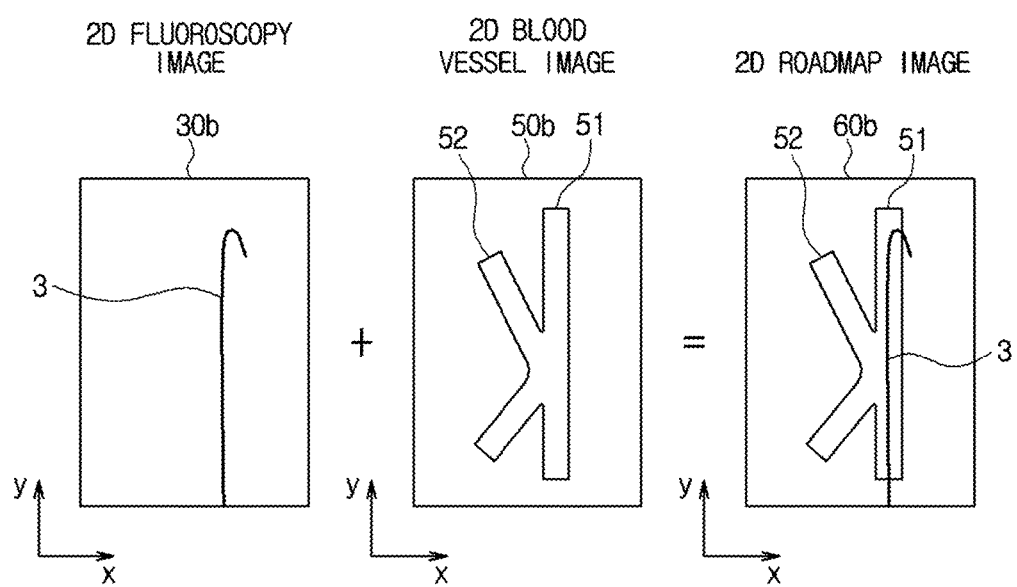

The X-ray imaging apparatus 100 may output an alarm to guide the operator to keep inserting the surgical tool 3 into the subject. The alarm may be output by the controller 140 (see FIG. 2). The operator who recognized the alarm may keep inserting the surgical tool 3 into the subject. Then, the location of the surgical tool 3 may change in a 2D fluoroscopy image that is acquired in real time. For example, the location of the surgical tool 3 may change as shown in a 2D fluoroscopy image 30*b* of FIG. 8C. FIG. 8C also shows a 2D blood vessel image 50*b*.

Figure 8D:
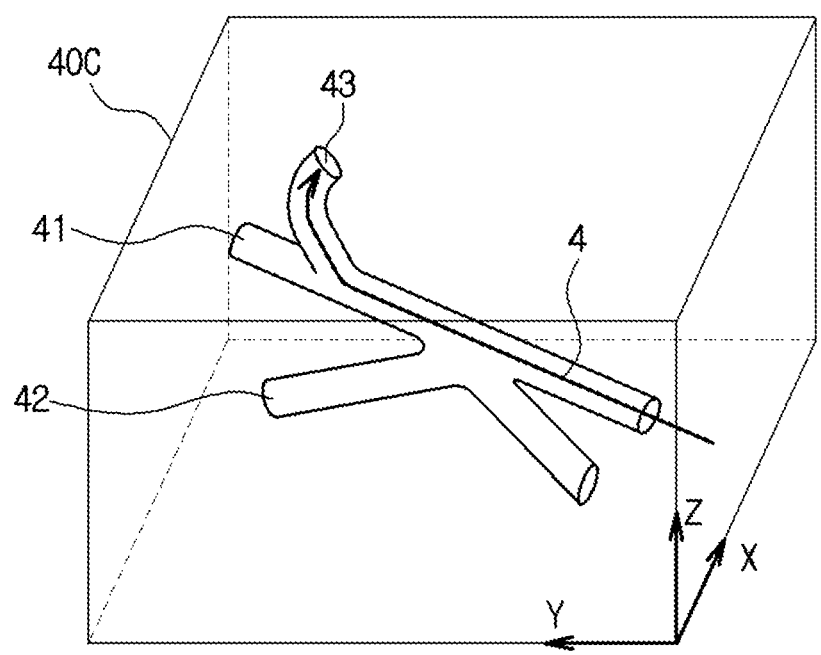

If the location of the surgical tool 3 keeps changing, a 2D roadmap image may also change. For example, a 2D roadmap image 60*b* as shown in FIG. 8C may be acquired. Then, a blood vessel corresponding to the location of the surgical tool 3 may be detected from the 2D roadmap image 60*b* shown in FIG. 8C, and blood vessel candidates corresponding to the location of the detected blood vessel may be detected from a 3D blood vessel image. In the case of the 3D blood vessel image 40 shown in FIG. 8A, the third blood vessel 43 may be detected as a blood vessel candidate. If a blood vessel candidate is detected, an alarm may be no longer output. The detected blood vessel candidate may be determined as a blood vessel path corresponding to a moving path of the surgical tool 3, and the moving path 4 of the surgical tool 3 may be marked as an identifier in the blood vessel path, as shown in FIG. 8D. A 3D roadmap image 40C as shown in FIG. 8D may be displayed through the display 170.

Figure 9:
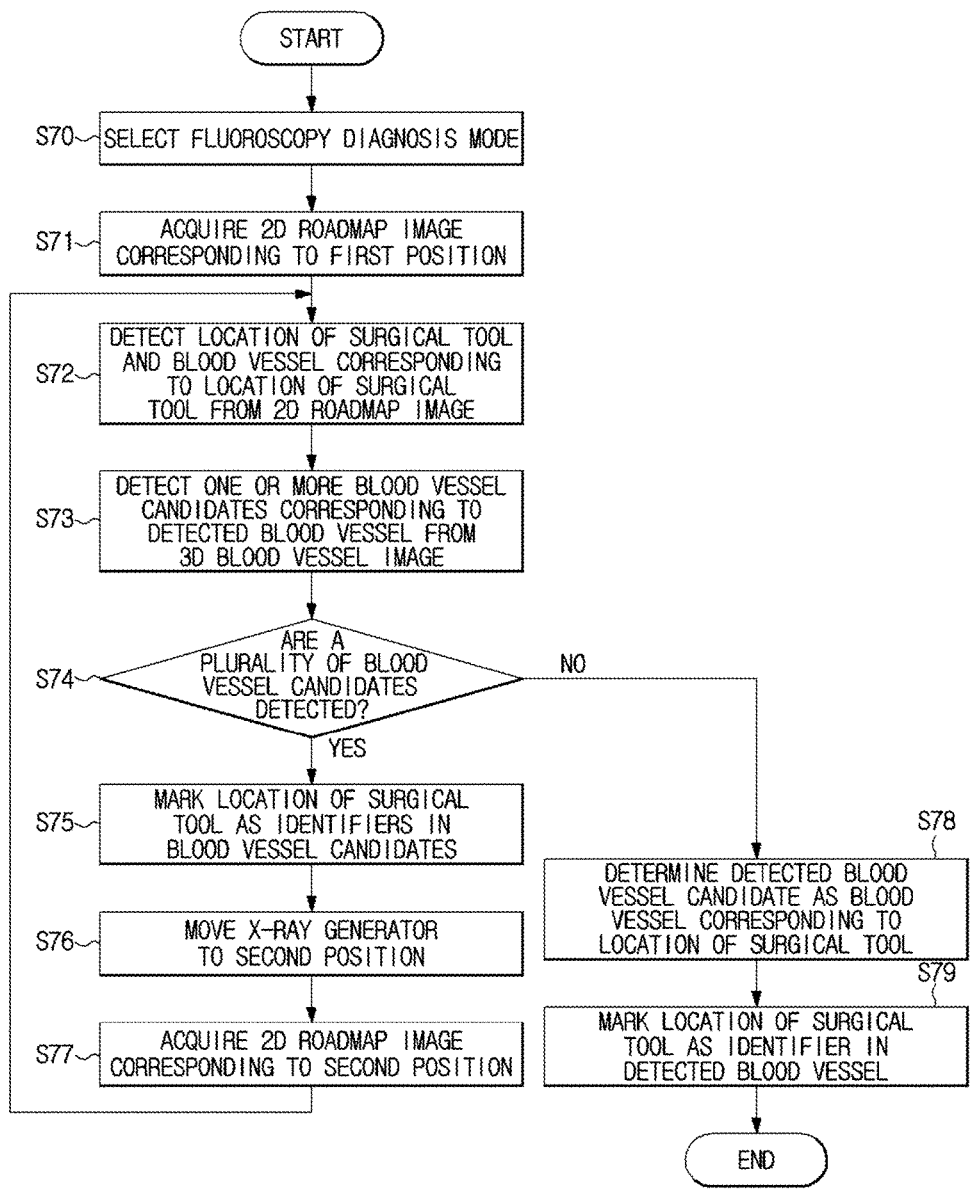
FIG. 9 is a flowchart illustrating a control method of an X-ray imaging apparatus according to the method illustrated in FIGS. 7A to 7F, according to an exemplary embodiment of the present disclosure.

FIG. 9 is a flowchart illustrating a control method of the X-ray imaging apparatus 100 according to the method illustrated in FIGS. 7A to 7F, according to an exemplary embodiment of the present disclosure. The following description will be given with reference to FIGS. 2, 7A to 7F, and 9.

Before the control method is described, it is assumed that a 3D blood vessel image 40 has been acquired in advance by the X-ray imaging apparatus 100 or an external device, and stored in the storage unit 180.

If a fluoroscopy diagnosis mode is selected (operation S70), a 2D roadmap image corresponding to a first position 1 may be acquired (operation S71). Operation S71 may include operations of: projecting the 3D blood vessel image 40 onto a 2D plane perpendicular to the first position 1 to acquire a 2D blood vessel image 50 corresponding to the first position 1; continuing to irradiate X-rays to a subject to acquire a 2D fluoroscopy image 30 corresponding to the first position 1 in real time while the X-ray generator 110 is located at the first position 1; and overlapping the 2D fluoroscopy image 30 corresponding to the first position 1 with the 2D blood vessel image 50 corresponding to the first position 1 to acquire a 2D roadmap image 60 corresponding to the first position 1. The 2D roadmap image 60 acquired at operation S71 may be displayed through the first display 171 of the display 170.

Thereafter, a location of a surgical tool 3 and a blood vessel corresponding to the location of the surgical tool 3 may be detected from the 2D roadmap image 60 (operation S72). Because the surgical tool 3 appears with dark brightness in the 2D roadmap image 60, the location of the surgical tool 3 may be detected by detecting pixels having brightness lower than a reference value.

Then, one or more blood vessel candidates corresponding to the detected blood vessel may be detected from the 3D blood vessel image 40 (operation S73). The blood vessel candidates corresponding to the detected blood vessel may be detected with reference to a mapping table acquired during operation of projecting the 3D blood vessel image 40 to the 2D blood vessel image 50.

Then, it may be determined whether a plurality of blood vessel candidates has been detected (operation S74).

If it is determined that a blood vessel candidate has been detected ("NO" in operation S74), the detected blood vessel candidate may be determined as a blood vessel corresponding to the location of the surgical tool 3 (operation S78).

Then, the location of the surgical tool 3 may be marked as an identifier in the determined blood vessel (operation S79). The identifier may be a solid line.

If it is determined that a plurality of blood vessel candidates have been detected ("YES" in operation S74), the location of the surgical tool 3 may be marked as identifiers in the detected blood vessel candidates (operation S75). The identifiers may be dotted lines. Because a blood vessel corresponding to the location of the surgical tool 3 among the detected blood vessel candidates has not yet been determined, identifiers that are different from an identifier (e.g., a thick solid line) indicating the actual location of the surgical tool 3 may be displayed in the blood vessel candidates. A 3D roadmap image 40B in which the identifiers have been displayed may be displayed through the second display 172 of the display 170.

Thereafter, the X-ray generator 110 may move to a second position 2 (operation S76). Because the position of the X-ray generator 110 changes, the position of the X-ray detector 120 may also change. The position of the X-ray generator 110 may change within an angle range between 10 degrees and 90 degrees. An angle by which the position of the X-ray generator 110 changes when the X-ray generator 110 moves one time may be set by an operator before X-ray scanning.

Then, a 3D roadmap image corresponding to the second position 2 may be acquired (operation S77). Operation S77 may include operations of: projecting the 3D blood vessel image 40 onto a 2D plane perpendicular to the second position 2 to acquire a 2D blood vessel image 50*a*; continuing to irradiate X-rays to the subject to acquire a 2D fluoroscopy image 30*a* in real time while the X-ray generator 110 is located at the second position 2; and overlapping the 2D fluoroscopy image 30*a* corresponding to the second position 2 with the 2D blood vessel image 50*a* corresponding to the second position 2 to acquire a 2D roadmap image 60*a* corresponding to the second position 2.

If the 2D roadmap image 60*a* corresponding to the second position 2 is acquired, operations S72 and S73 may be repeatedly performed. Then, it may be again determined whether a plurality of blood vessel candidates has been detected from the 3D blood vessel image 40 (operation S74).

If it is determined that a blood vessel candidate has been detected from the 3D blood vessel image 40, the X-ray generator 110 may return to its previous position. That is, the X-ray generator 110 may move from the second position 2 to the first position 1. Then, the blood vessel candidate detected from the 3D blood vessel image 40 may be determined as a blood vessel corresponding to the location of the surgical tool 3 (operation S78), and the location of the surgical tool 3 may be marked as an identifier (e.g., a solid line) in the determined blood vessel (operation S79).

A 3D roadmap image 40C in which the location of the surgical tool 3 is marked as the identifier in the determined blood vessel may be displayed through the second display 172 of the display 170.

Figure 10:
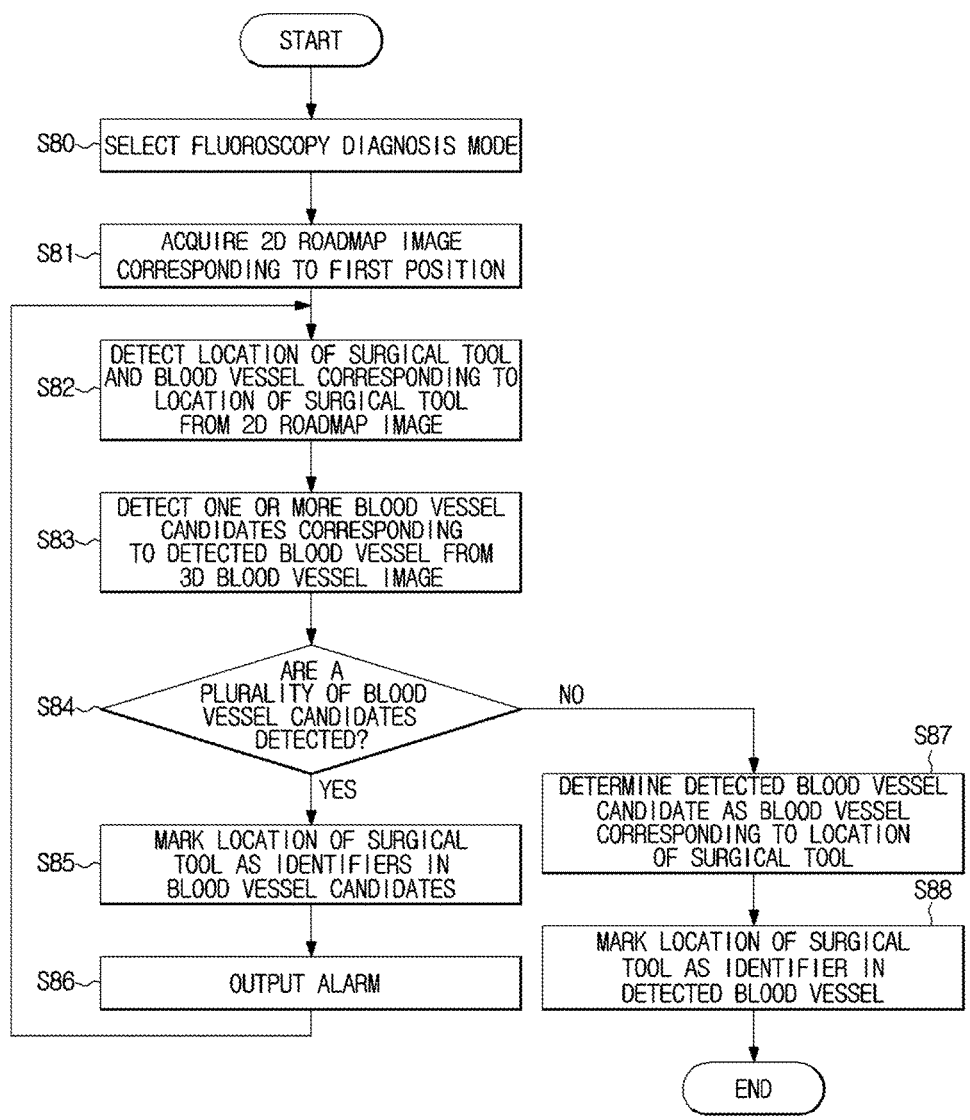
FIG. 10 is a flowchart illustrating a control method of an X-ray imaging apparatus according to the method illustrated in FIGS. 8A to 8D, according to an exemplary embodiment of the present disclosure.

FIG. 10 a flowchart illustrating a control method of the X-ray imaging apparatus 100 according to the method illustrated in FIGS. 8A to 8D, according to an embodiment of the present disclosure.

Before the control method is described, it is assumed that a 3D blood vessel image 40 has been acquired in advance by the X-ray imaging apparatus 100 or an external device, and stored in the storage unit 180.

If a fluoroscopy diagnosis mode is selected (operation S80), a 2D roadmap image 60 corresponding to first position 1 may be acquired (operation S81). Operation S81 may include operations of: projecting the 3D blood vessel image 40 onto a 2D plane perpendicular to the first position 1 to acquire a 2D blood vessel image 50 corresponding to the first position 1; continuing to irradiate X-rays to a subject to acquire a 2D fluoroscopy image 30 corresponding to the first position 1 in real time while the X-ray generator 110 is located at the first position 1; and overlapping the 2D fluoroscopy image 30 corresponding to the first position 1 with the 2D blood vessel image 50 corresponding to the first position 1 to acquire the 2D roadmap image 60 corresponding to the first position 1. The 2D roadmap image 60 acquired in operation S81 may be displayed through the first display 171 of the display 170.

Thereafter, a location of a surgical tool 3 and a blood vessel corresponding to the location of the surgical tool 3 may be detected from the 2D roadmap image 60 (operation S82). Because the surgical tool 3 appears with dark brightness in the 2D roadmap image 60, the location of the surgical tool 3 may be detected by detecting pixels having brightness lower than a reference value.

Then, one or more blood vessel candidates corresponding to the detected blood vessel may be detected from the 3D blood vessel image 40 (operation S83). The blood vessel candidates corresponding to the detected blood vessel may be detected with reference to a mapping table acquired during operation of projecting the 3D blood vessel image 40 to the 2D blood vessel image 50.

Then, it may be determined whether a plurality of blood vessel candidates has been detected (operation S84).

If it is determined that a blood vessel candidate has been detected ("NO" in operation S84), the detected blood vessel candidate may be determined as a blood vessel corresponding to the location of the surgical tool 3 (operation S87).

Then, the location of the surgical tool 3 may be marked as an identifier in the determined blood vessel (operation S88). The identifier may be a solid line.

If it is determined that a plurality of blood vessel candidates have been detected ("YES" in operation S84), the location of the surgical tool 3 may be marked as identifiers in the detected blood vessel candidates (operation S85). The identifiers may be dotted lines. Because a blood vessel corresponding to the location of the surgical tool 3 among the detected blood vessel candidates has not yet been determined, identifiers that are different from an identifier (e.g., a thick solid line) indicating the actual location of the surgical tool 3 may be displayed in the blood vessel candidates.

Thereafter, an alarm may be output (operation S86). That is, an alarm for notifying an operator that a plurality of blood vessel candidates has been detected may be output. The alarm may be at least one of sound, vibration, and an image. The operator who recognized the alarm may keep inserting the surgical tool 3 into the subject.

If the surgical tool 3 is further inserted, the location of the surgical tool 3 may also change in a 2D fluoroscopy image 30b that is acquired in real time. As the location of the surgical tool 3 changes in the 2D fluoroscopy image 30b, a 2D roadmap image 60b may also change. If the changed 2D roadmap image 60b is acquired, operations S82 and S83 may be repeatedly performed. Thereafter, it may be again determined whether a plurality of blood vessel candidates has been detected from the 3D blood vessel image 40 (operation S84).

If it is determined that a blood vessel candidate has been detected from the 3D blood vessel image 40, the alarm may be no longer output. Then, the detected blood vessel candidate may be determined as a blood vessel corresponding to the location of the surgical tool 3 (operation S87), and the location of the surgical tool 3 may be marked as an identifier (e.g., a solid line) in the determined blood vessel (operation S88).

A 3D roadmap image 40C in which the location of the surgical tool 3 is marked as the identifier in the determined blood vessel may be displayed through the second display 172 of the display 170.

Embodiments of the present disclosure have been described above. In the embodiments described above, some of components constituting the X-ray imaging apparatus 100 may be implemented as a "module". Here, the term 'module' means, but is not limited to, a software and/or hardware component, such as a Field Programmable Gate Array (FPGA) or Application Specific Integrated Circuit (ASIC), which performs certain tasks. A module may advantageously be configured to reside on the addressable storage medium and configured to execute on one or more processors.

Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The operations provided for in the components and modules may be combined into fewer components and modules or further separated into additional components and modules. In addition, the components and modules may be implemented such that they execute one or more CPUs in a device.

With that being said, and in addition to the above described embodiments, embodiments of the present disclosure can thus be implemented through computer readable code/instructions in/on a medium, e.g., a computer readable medium, to control at least one processing element to implement any above described embodiment. The medium can correspond to any medium/media permitting the storing and/or transmission of the computer readable code. The computer-readable code can be recorded on a medium or transmitted through the Internet. The medium may include Read Only Memory (ROM), Random Access Memory (RAM), Compact Disk-Read Only Memories (CD-ROMs), magnetic tapes, floppy disks, and optical recording medium. Also, the medium may be a non-transitory computer-readable medium. The media may also be a distributed network, so that the computer readable code is stored or transferred and executed in a distributed fashion. Still further, as only an example, the processing element could include at least one processor or at least one computer processor, and processing elements may be distributed and/or included in a single device.

While exemplary embodiments have been described with respect to a limited number of embodiments, those skilled in the art, having the benefit of this disclosure, will appreciate that other embodiments can be devised which do not depart from the scope as disclosed herein. Accordingly, the scope should be limited only by the attached claims.

What is claimed is:

1. An X-ray imaging apparatus comprising:
an X-ray generator configured to direct X-rays to a subject;
an X-ray detector that detects X-rays generated by the X-ray generator and outputs image data;

an image processor that receives the image data output by the X-ray detector and produces a plurality of 2-dimensional (2D) images of the subject, wherein the image processor is configured to:
generate a 3-Dimensional (3D) image of the subject from the plurality of 2D images of the subject,
generate a 3D blood vessel image by extracting blood vessel information from the 3D image of the subject,
generate a 2D blood vessel image by projecting the 3D blood vessel image onto a 2D plane,
overlap the 2D blood vessel image with a 2D fluoroscopy image to acquire a 2D roadmap image corresponding to a first position,
detect a location of a surgical tool from the 2D roadmap image corresponding to the first position,
detect a blood vessel corresponding to the location of the surgical tool from the 3D blood vessel image,
mark the location of the surgical tool with an identifier in the detected blood vessel; and
a display configured to display the 2D roadmap image, the detected blood vessel, and the identifier.

2. The X-ray imaging apparatus according to claim 1, wherein the image processor is further configured to generate the 2D fluoroscopy image from irradiated X-rays from the X-ray generator, when the X-ray generator is located at the first position.

3. The X-ray imaging apparatus according to claim 1, wherein the image processor is further configured to:
detect the location of the surgical tool and the blood vessel corresponding to the location of the surgical tool from the 2D roadmap image corresponding to the first position; and
detect one or more blood vessel candidates corresponding to the detected blood vessel, from the 3D blood vessel image.

4. The X-ray imaging apparatus according to claim 3, wherein, if a single blood vessel candidate is detected from the 3D blood vessel image, the image processor is further configured to determine that the detected blood vessel candidate is the blood vessel corresponding to the location of the surgical tool.

5. The X-ray imaging apparatus according to claim 3, further comprising:
a controller configured to move the X-ray generator from the first position to a second position in response to a plurality of blood vessel candidates being detected from the 3D blood vessel image.

6. The X-ray imaging apparatus according to claim 5, wherein the image processor is further configured to determine a blood vessel corresponding to the location of the surgical tool from among the plurality of blood vessel candidates, based on a second 2D roadmap image corresponding to the second position, and
wherein the image processor is further configured to overlap a second 2D blood vessel image with a second 2D fluoroscopy image to acquire the second 2D roadmap image corresponding to the second position.

7. The X-ray imaging apparatus according to claim 6, further comprising:
wherein the image processor is configured to generate the second 2D fluoroscopy image from irradiated X-rays from the X-ray generator, when the X-ray generator is located at the second position;
wherein the image processor is further configured to generate a second 3-Dimensional (3D) image of the subject;
wherein the image processor is further configured to generate a second 3D blood vessel image by extracting blood vessel information from the 3D image of the subject; and
wherein the image processor is further configured to generate the second 2D blood vessel image by projecting the second 3D blood vessel image onto a 2D plane perpendicular to the second position.

8. The X-ray imaging apparatus according to claim 3, further comprising:
a controller configured to output an alarm for guiding an operator inserting the surgical tool into a subject if a plurality of blood vessel candidates are detected from the 3D blood vessel image.

9. The X-ray imaging apparatus according to claim 3, wherein, if a plurality of blood vessel candidates are detected from the 3D blood vessel image, the image processor is further configured to display the plurality of blood vessel candidates differently from remaining blood vessels in the 3D blood vessel image.

10. A method of controlling an X-ray imaging apparatus, the method comprising:
generating X-rays with an X-ray generator and directing the X-rays to a subject;
detecting the X-rays with an X-ray detector and outputting image data;
producing, using an image processor, a plurality of 2-dimensional (2D) images of the subject from the image data;
generating, using the image processor, a 3-Dimensional (3D) image of the subject from the plurality of (2D) images of the subject;
generating, using the image processor, a 3D blood vessel image by extracting blood vessel information from the 3D image of the subject;
generating, using the image processor, a 2D blood vessel image by projecting the 3D blood vessel image onto a 2D plane;
overlapping, using the image processor, the 2D blood vessel image with a 2D fluoroscopy image to acquire a 2D roadmap image corresponding to a first position;
detecting, using the image processor, a location of a surgical tool from the 2D roadmap image corresponding to the first position;
detecting, using the image processor, a blood vessel corresponding to the location of the surgical tool from the 3D blood vessel image;
marking the location of the surgical tool with an identifier in the detected blood vessel; and
displaying the 2D roadmap image, the detected blood vessel, and the identifier on a display.

11. The method according to claim 10, further comprising:
generating, using the image processor, the 2D fluoroscopy image from irradiated X-rays from the X-ray generator, when the X-ray generator is located at the first position.

12. The method according to claim 10, wherein the detecting of the blood vessel corresponding to the location of the surgical tool from the 3D blood vessel image comprises:
detecting one or more blood vessel candidates corresponding to the detected blood vessel from the 3D blood vessel image.

13. The method according to claim 12, further comprising:
determining that the detected blood vessel candidate is the blood vessel corresponding to the location of the surgical tool in response to a single blood vessel candidate being detected from the 3D blood vessel image.

14. The method according to claim 12, further comprising:
moving the X-ray generator from the first position to a second position in response to a plurality of blood vessel candidates being detected from the 3D blood vessel image; and
determining a blood vessel corresponding to the location of the surgical tool from among the plurality of blood vessel candidates, based on a second 2D roadmap image corresponding to the second position.

15. The method according to claim 14, further comprising:
generating a second 2D fluoroscopy image from irradiated X-rays from the X-ray generator, when the X-ray generator is located at the second position;
generating a second 3D image of the subject;
generating a second 3D blood vessel image by extracting blood vessel information from the 3D image of the subject; and
generating a second 2D blood vessel image by projecting the second 3D blood vessel image onto a 2D plane perpendicular to the second position.

16. The method according to claim 12, further comprising:
outputting an alarm for guiding an operator inserting the surgical tool into the subject in response to a plurality of blood vessel candidates being detected from the 3D blood vessel image.

17. The method according to claim 12, further comprising:
displaying a plurality of blood vessel candidates differently from remaining blood vessels in the 3D blood vessel image in response to the plurality of blood vessel candidates being detected from the 3D blood vessel image.

18. An X-ray imaging apparatus comprising:
an X-ray generator configured to direct X-rays to a subject;
an X-ray detector that detects X-rays generated by the X-ray generator and outputs image data;
an image processor that receives the image data output by the X-ray detector and produces a plurality of 2-dimensional (2D) images of the subject, and is configured to:
generate a 3-Dimensional (3D) image of the subject from the plurality of 2D images of the subject,
generate a 3D blood vessel image by extracting blood vessel information from the 3D image of the subject,
generate a 2D blood vessel image by projecting the 3D blood vessel image onto a 2D plane,
detect a location of a surgical tool in a blood vessel in the 2D blood vessel image, acquire a 2D roadmap image corresponding to a first position by overlapping the 2D blood vessel image with a 2D fluoroscopy image, and
mark the location of the surgical tool with an identifier in the blood vessel; and
a display configured to display the 2D roadmap image, the blood vessel, and the identifier.

19. The X-ray imaging apparatus of claim 18:
wherein the X-ray generator is configured to move from the first position to a second position,
wherein the image processor is further configured to detect the location of the surgical tool in the blood vessel of a second 2D blood vessel image corresponding to the second position, and
wherein the image processor is further configured to acquire a second 2D roadmap image corresponding to the second position by overlapping the second 2D blood vessel image with a second 2D fluoroscopy image.

* * * * *